(12) United States Patent
Aoki et al.

(10) Patent No.: US 7,595,183 B2
(45) Date of Patent: Sep. 29, 2009

(54) **CATHEPSINS L-LIKE CYSTEINE PROTEASE DERIVED FROM NORTHERN SHRIMP (*PANDALUS EOUS*)**

(75) Inventors: Hitoshi Aoki, Chiba (JP); Shugo Watabe, Tokyo (JP); Md. Nazmul Ahsan, Tokyo (JP)

(73) Assignee: Nichirei Corporation, Tokyo (JP)

( * ) Notice: Subject to any disclaimer, the term of this patent is extended or adjusted under 35 U.S.C. 154(b) by 1353 days.

(21) Appl. No.: 10/849,162

(22) Filed: May 20, 2004

(65) Prior Publication Data

US 2004/0253707 A1 Dec. 16, 2004

Related U.S. Application Data

(63) Continuation of application No. PCT/JP03/07661, filed on Jun. 17, 2003.

(60) Provisional application No. 60/471,733, filed on May 20, 2003.

(30) Foreign Application Priority Data

Jun. 17, 2002 (JP) .............................. 2002-175773

(51) Int. Cl.
*C12N 9/64* (2006.01)
*C12N 15/57* (2006.01)
*C12N 15/79* (2006.01)
*C12N 15/81* (2006.01)

(52) U.S. Cl. .................. 435/226; 435/69.1; 435/252.3; 435/254.23; 435/320.1; 536/23.2

(58) Field of Classification Search ....................... None
See application file for complete search history.

(56) References Cited

U.S. PATENT DOCUMENTS

| | | | | |
|---|---|---|---|---|
| 5,736,357 | A * | 4/1998 | Bromme et al. | ............ 435/69.1 |
| 5,776,759 | A * | 7/1998 | Bandman et al. | ............ 435/226 |
| 5,965,129 | A * | 10/1999 | Bandman et al. | ......... 424/94.65 |
| 6,033,893 | A * | 3/2000 | Bandman et al. | ............ 435/212 |
| 6,475,485 | B1 * | 11/2002 | Bandman et al. | ......... 424/94.63 |
| 6,544,767 | B1 * | 4/2003 | Bromme et al. | ............ 435/226 |
| 6,620,606 | B2 * | 9/2003 | Bandman et al. | ............ 435/219 |
| 6,627,605 | B1 * | 9/2003 | Bandman et al. | ............. 514/12 |
| 6,855,811 | B2 * | 2/2005 | Bandman et al. | .......... 530/387.9 |
| 7,045,333 | B1 * | 5/2006 | Bandman et al. | ............ 435/226 |

OTHER PUBLICATIONS

Laycook Maurice V. et al., Molecular cloning of three cDNAs that encode cysteine proteinases in the digestive gland of the American lobster (*Homarus americanus*), FEBS Lett. 292 (1,2), 115-120 (1991).

(Continued)

*Primary Examiner*—Rebecca E Prouty
*Assistant Examiner*—William W Moore
(74) *Attorney, Agent, or Firm*—Sughrue Mion, PLLC

(57) ABSTRACT

The object of the present invention is to find and produce cathepsin L having high activity under neutral to alkaline conditions and at a low temperature range. The present inventors succeeded in discovering novel cathepsin L having activity even at a low temperature range from hepatopancreas of Japanese northern shrimp. The present inventors further determined the gene sequence encoding said novel cathepsin L, thus enabling production thereof by genetic recombination.

7 Claims, 18 Drawing Sheets

OTHER PUBLICATIONS

Le Boulay C et al., 'Molecular cloning and sequencing of two cDNAs encoding cathepsin L-related cysteine poteinsases in the nervous system and in the stomach of the Norway lobster (*Nephrops norvegicus*)' Comp. Biochem. Physiol., 111B(3), 353-359 (1995).

Le Boulay C. et al., 'Cloning and expression of cathepsin L-like proteinases in the hepatopancreas of the shrimp *Penaeus vannamei* during the intermolt cycle' J.Comp.Physiol.B, 166, 310-318 (1996).

Joseph Loren J. et al., 'Complete Nucleotide and Deduced Amino Acid Sequence of Human and Murine Preprocathepsin L', J.Clin. Invest., 81(5)1621-1629 (1988).

Berri Mustapha et al., 'Purification and Characterization of a New Potential In Vivo Inhibitor of Cathepsin L From Bovine Skeletal Muscle', Comparative Biochemistry and Physiology, 119B(2), 283-288 (1998).

* cited by examiner

Fig. 1

```
TGAGTCAGTTCTGCTCAACTCTGATACGATGAAGGTTCTTCTTTTCCTGTGTGGTCTG      58
                              M  K  V  L  L  F  L  C  G  L      10
GCCATAGTCGCCGCTAGTGAATGGGAAAACTTCAAGTTGACCCATGCTAAAGTTTACACC    118
 A  I  V  A  A  S  E  W  E  N  F  K  L  T  H  A  K  V  Y  T    30
CATGGCAAGGAAGATCTTTACAGGAGGTCCATCTTTGAGAACAACCAGAAGGTTGTCGAG    178
 H  G  K  E  D  L  Y  R  R  S  I  F  E  N  N  Q  K  V  V  E    50
GAACACAATGAACGATTCCGTCAGGGACTTGTCACCTTCGACCTCAAGATGAACAGATTC    238
 E  H  N  E  R  F  R  Q  G  L  V  T  F  D  L  K  M  N  R  F    70
GGAGATATGACGACAGAGGAGTTTGTATCCCAGATGACCGGGCTCAACAAAGTAGAGAGG    298
 G  D  M  T  T  E  E  F  V  S  Q  M  T  G  L  N  K  V  E  R    90
ACCGTTGGTAAGGTGTTCGCTCACTACCCTGAAGTAGAAAGGGCTGACACTGTTGACTGG    358
 T  V  G  K  V  F  A  H  Y  P  E  V  E  R  A  D  T  V  D  W   110
AGAGACAAAGGAGCTGTGACCCCAGTTAAGGATCAGGGTCAGTGTGGATCATGCTGGGCC    418
 R  D  K  G  A  V  T  P  V  K  D  Q  G  Q  C  G  S  C  W  A   130
TTCTCTACCACTGGAGCTCTGGAAGGAGCACATTTCCTGAAACACGGCGATTTAGTCAGT    478
 F  S  T  T  G  A  L  E  G  A  H  F  L  K  H  G  D  L  V  S   150
CTGTCCGAACAAAATCTGGTCGATTGCTCAACTGAGAACAGTGGCTGTAACGGCGGTGTG    538
 L  S  E  Q  N  L  V  D  C  S  T  E  N  S  G  C  N  G  G  V   170
GTCCAATGGGCCTACGACTACATCAAGTCCAACAACGGAATTGATACTGAATCTTCATAC    598
 V  Q  W  A  Y  D  Y  I  K  S  N  N  G  I  D  T  E  S  S  Y   190
CCCTACGAAGCTCAAGATTTAACTTGTCGATTCGACGCTGCACACGTTGGTGCTACCGTT    658
 P  Y  E  A  Q  D  L  T  C  R  F  D  A  A  H  V  G  A  T  V   210
ACTGGATACGCAGATATCCCTTATGCTGATGAAGTGACCCAGGCCTCAGCTGTCCATGAT    718
 T  G  Y  A  D  I  P  Y  A  D  E  V  T  Q  A  S  A  V  H  D   230
GATGGTCCAGTCAGCGTCTGTATTGATGCTGGACACAATTCCTTCCAGTTGTACAGCTCA    778
 D  G  P  V  S  V  C  I  D  A  G  H  N  S  F  Q  L  Y  S  S   250
GGTGTGTACTACGAGCCTAACTGCAATCCTAGCTCTATCAACCACGCTGTGTTGCCCGTA    838
 G  V  Y  Y  E  P  N  C  N  P  S  S  I  N  H  A  V  L  P  V   270
GGATACGGAACAGAGGAAGGCAGTGACTACTGGCTCATCAAGAACTCTTGGGGAACTGGC    898
 G  Y  G  T  E  E  G  S  D  Y  W  L  I  K  N  S  W  G  T  G   290
TGGGGTCTGAGTGGATACATGAAGCTCACAAGGAACAAGAGCAATCATTGTGGTGTCGCC    958
 W  G  L  S  G  Y  M  K  L  T  R  N  K  S  N  H  C  G  V  A   310
ACCCAATCTTGTTACCCTAATGTCTAAGAGCTCAATTTAAGACATGGTTTTCCACTTAAA   1018
 T  Q  S  C  Y  P  N  V                                        318
CAACGGAGGTAATGTTTAACCATTTCAAAAACACCTCAGGAAAGCCTTATGGATAAAAGT   1078
AATGGATATCTTCAAACAATTTTCCACTGAATTTTCTTGTGTGACGATAAAACATCTACT   1138
TCCGCCATTTTAAGATTACACCTGACTCAAACTATACATATTAATGTGTGTAGCATTCTA   1198
GTAGAAAATAAAGAAAGCATTACAAAATAAAAAAAAAAAAAAAAAAA                1246
```

Fig. 2

```
CACTTTAGCAAGATGAGGTCTCTGTTTCTTATCCTTCTCGGGCTGGCTGCGGTCTCCGCC      60
             M  R  S  L  F  L  I  L  L  G  L  A  A  V  S  A    16
ATTGGAGAATGGGAAAACTTCAAGACGAAGTTTGGCAAGAAGTATGCCAACTCAGAAGAG     120
 I  G  E  W  E  N  F  K  T  K  F  G  K  K  Y  A  N  S  E  E    36
GAGAGTCACAGAATGTCTGTTTTCATGGACAAACTGAAGTTCATTCAGGAGCACAATGAA     180
 E  S  H  R  M  S  V  F  M  D  K  L  K  F  I  Q  E  H  N  E    56
CGATACGATAAGGGAGAAGTCACTTATTGGCTGAAAATCAACAACTTCTCCGATTTGACC     240
 R  Y  D  K  G  E  V  T  Y  W  L  K  I  N  N  F  S  D  L  T    76
CACGAAGAGGTCTTGGCCACCAAGACTGGAATGACCAGGAGACGACACCCTCTTTCCGTA     300
 H  E  E  V  L  A  T  K  T  G  M  T  R  R  R  H  P  L  S  V    96
TTGCCCAAATCTGCCCCAACCACACCAATGGCCGCAGACGTTGACTGGAGGAATAAGGGG     360
 L  P  K  S  A  P  T  T  P  M  A  A  D  V  D  W  R  N  K  G   116
GCTGTCACCCCCGTCAAGGATCAGGGACAATGCGGATCATGCTGGGCTTTCTCAGCTGTC     420
 A  V  T  P  V  K  D  Q  G  Q  C  G  S  C  W  A  F  S  A  V   136
GCCGCCTTGGAAGGAGCGCACTTCCTGAAGACCGGAGATTTGGTCAGCCTGTCTGAACAG     480
 A  A  L  E  G  A  H  F  L  K  T  G  D  L  V  S  L  S  E  Q   156
AATTTGGTTGACTGCTCTTCGTCTTACGGTAACCAAGGATGTAATGGTGGATGGCCATAC     540
 N  L  V  D  C  S  S  S  Y  G  N  Q  G  C  N  G  G  W  P  Y   176
CAAGCTTATCAATACATCATTGCCAATCGTGGCATTGACACCGAATCGTCATACCCTTAC     600
 Q  A  Y  Q  Y  I  I  A  N  R  G  I  D  T  E  S  S  Y  P  Y   196
AAGGCAATTGATGACAATTGCCGATATGATGCCGGAAACATCGGCGCCACCGTCAGCAGT     660
 K  A  I  D  D  N  C  R  Y  D  A  G  N  I  G  A  T  V  S  S   216
TATGTCGAACCAGCTTCAGGAGATGAGTCCGCACTTCAGCATGCTGTCCAGAATGAAGGA     720
 Y  V  E  P  A  S  G  D  E  S  A  L  Q  H  A  V  Q  N  E  G   236
CCCGTCAGCGTCTGCATTGATGCTGGTCAATCATCTTTCGGTAGTTACGGAGGAGGTGTT     780
 P  V  S  V  C  I  D  A  G  Q  S  S  F  G  S  Y  G  G  G  V   256
TACTATGAACCAAACTGCGATTCCTGGTACGCCAACCATGCCGTGACAGCCGTCGGCTAC     840
 Y  Y  E  P  N  C  D  S  W  Y  A  N  H  A  V  T  A  V  G  Y   276
GGCACCGACGCCAACGGAGGAGATTACTGGATCGTCAAGAACTCGTGGGGTGCATGGTGG     900
 G  T  D  A  N  G  G  D  Y  W  I  V  K  N  S  W  G  A  W  W   296
GGAGAGAGTGGCTACATCAAGATGGCCAGAAACAGGGACAACAACTGTGCCATTGCTACC     960
 G  E  S  G  Y  I  K  M  A  R  N  R  D  N  N  C  A  I  A  T   316
TATAGTGTCTACCCTGTTGTTTAAGATCTTTTATTGACACTCACAATGATTTCTTTCCA    1020
 Y  S  V  Y  P  V  V                                            323
TCATTTATCATTGGGGAACTTTTAATATTCATTTGGGGTTTTCATTTGATATTTTGTGTA    1080
AGTCTCAGTCAATCCCATTAGACATGTTTTGTTACGGTGGATTCTTAAGTCAACCTTTGA    1140
ATCAAACACTTTTGTCAAATTACAATGAACACATCCAACAGATGATGATACATATGAAAA    1200
TAAAGATACAACAGATAAAAAAAAAAAAAAAAAAAAAAAAAA                      1242
```

FIG. 8

|  | 1 | 10 | 20 | 30 | 40 | 50 | 60 | 70 | 80 |
|---|---|---|---|---|---|---|---|---|---|
| Northern shrimp 1 | --DTVDWRDK | GAVTPVKDQG | QCGSCWAFST | TGALEGAHFL | KHGDLVSLSE | QNLVDCST-E--N | S-SYG.Q. | SGCNGGVVQW | AYDYIKSNNGI |
| Northern shrimp 2 | -AAD....N. | ........... | .......... | ..A.VA.... | .T........ | ..........  | AGGSYY.Q. | .WPYQ...Q. | .IA.R...... |
| American lobster 1 | -STE....T. | ........... | .......... | .....GI.Q. | .T.R...... | ..........Q. | R-PYGP.Q. | .W.ER..IM. | VRD.G.V.... |
| American lobster 2 | -ATE....T. | ........... | .......... | .....S..Q. | .T.S.I..A. | ..........Q. | -DYG..D.G. | .WMND...F. | ..A........ |
| American lobster 3 | -AAD....T. | ......AL... | ..........E | .....A.... | .NDE...... | ..........Q. | D-KFG..M.M | .WMTS...F. | ..D.G...... |
| Tropical shrimp 1 | LPEK....T. | ........... | .......... | .....S..Q. | .D.K...... | ..........Q. | D-KFG..M.M | .LMDQ...FR. | ..A.K...... |
| Tropical shrimp 2 | LPKE....T. | ........... | .......... | .....S..Q. | .D.K...... | ..........Q. | AGGIYY.Q. | .LMDQ...FR. | ..A.K...... |
| Norway lobster 1 | -TTE....T. | ......C..H. | .......... | .....A..Q. | .Y.E....A. | ..........Q. | -YG....D.G | .W.NQ...FK. | ..A.G...... |
| Norway lobster 2 | -AAD....T. | ........... | .......... | .....A..Q. | .NNE...... | ..........E. | H-DQG..Q. | .WMTS...F. | ..D.G...... |
| Rat CatL | IPK.....E. | ......C.... | ..........N | .....A.S.C. | .QM....... | ..........Q. | DR---RS.Y. | .LMDF...FQ. | .E.G.L..... |
| Papain | IPEY....Q. | ........N. | ..........S. | ...A.VVTI.IIKI | RT.N.NEY. | E.L......... |  | .YPWS...LQLVAQY- |  |

|  | 90 | 100 | 110 | 120 | 130 | 140 | 150 | 160 |
|---|---|---|---|---|---|---|---|---|
| Northern shrimp 1 | DTESSYPYEA | QDLTCR-FDA | AHVGATVTGY | ADIPYADEVT | QASAVHDDGPV | SVCIDAGHNS | FQLYSSGVYY | EPNCNPSSINHA |
| Northern shrimp 2 | .........K. | I.DN..-Y. | .GNI...... | VG.AQGS.SA | LKT.TR.I.I | .A...S.R. | .GS.GG... | .DSWYA..... |
| American lobster 1 | .......... | R.N...-.NS | NTI...C... | TN.ASGS.TG | LQQ.R.I..I | .T...A.S. | .S.YT.... | .S.SS.QLD.. |
| American lobster 2 | ........AA | R.GS...-.S | NS.A..CS.H | VEVQH-T.EA | LQE..SGV..I | .A...S.F. | .....FY.. | .S....YLD.. |
| American lobster 3 | .......... | E.RS...-.. | NSI.IC..S | V.VEHGS.SA | LKK..ATI..I | .G...SQST | HF.HT...H | .Q..S.TFLD.G |
| Tropical shrimp 1 | .......D.. | ..GK...-.. | SN.....D.. | V.VEHGS.SA | LKK..ATI..I | .A...SQP. | ...F.HD.. | DDH.SSTMLD.G |
| Tropical shrimp 2 | .......D.. | ..GK...-.. | SN.....D.. | VS.AQGS.SP | EVRRTTNT..I | .A...A.R. | ..S..... | EG.SSTMLD.G |
| Norway lobster 1 | .......... | R.N...-.NS | NS.A..CS.F | VEVQH-T.EA | LHE..S.I..I | .A...S.F. | ...F.... | .S.SS.QLD.G |
| Norway lobster 2 | .......S.E | K.GS...-.K-YR. | NSI...C..F | V...Q-Q.KA | LMK..ATV..I | AM..S.P. | L.F...I.. | KK.S.TNLD.G |
| Rat CatL | .......... | .SREK | EYAV.ND..F | V...Q-Q.KA | LLYSIAN-Q. | .VLE.AGKD | RG.IFV.G. | SSKDLD.G |
| Papain | HYRNT....G | VQRYG.SREK | GPYA.KTD.V | RQVQPYN.GA | LLYSIAN-Q. | .VLE.AGKD | RG.IFV.G. | -.G-NKVD.. |

|  | 170 | 180 | 190 | 200 | 210 |  |
|---|---|---|---|---|---|---|
| Northern shrimp 1 | VLPVGYGT-- | EE-GSDY WLIKNSWGTG | WGLSGYMKLT | RNKSNH--G | GVATQSCYPN V- | 213 |
| Northern shrimp 2 | TA........ | --DAN.G...IV. | ...AW...E. | .I.MA...RD.N-- | AI..Y.V..V . | - 217 |
| American lobster 1 | .A........ | -----S.G.Q.F .V. | ..A.S...E. | .I.MA...RN.N-- | .I..DA...T . | - 217 |
| American lobster 2 | .A........ | -----S.G.Q.F .V. | ..A.S...DA. | .I.MS...RN.N-- | .I..VAS..L . | - 216 |
| American lobster 3 | .A........ | -----T.STK...V. | ...SS...DA. | .I.MS...RD.N-- | .I.SEPS..T . | - 215 |
| Tropical shrimp 1 | .A........ | S---D.N.G.F .V. | ..N.S...DK. | .I.MS...RN.N-- | .I.S.AS..L . | - 218 |
| Tropical shrimp 2 | .A........ | E---T.K.EA. .V. | ..N.S...NK. | .IQMS...D.K.N-- | .I.S.AS..L . | - 218 |
| Norway lobster 1 | .A........ | -----S.G.Q.F .V. | ...S....SA. | .INMA...RN.N-- | .I..DAS..T . | - 217 |
| Norway lobster 2 | .A........ | -----T.STE...V. | ...S....DA. | .I.MS...RD.N-- | .I.SEPS..T . | - 215 |
| Rat CatL | .V........ | YEGTDSNKDK. ... | ...KE...MD. | .I.IA.KDRN.--- | L..AAS..I .N | 221 |
| Papain | AA........ | ------PN..I.. | .......EN. | IRIK...GTG.SYGVC | LY.S.F..V KN | 212 |

Fig. 9B

|      | NSL1 | NCP1 | NCP2 | LCP1 | LCP2 | LCP3 | PCP1 | PCP2 | RCL | HCL | RCS | HCS | RCK | HCK | HCH | RCH | HCB | RCB | Papain |
|------|------|------|------|------|------|------|------|------|-----|-----|-----|-----|-----|-----|-----|-----|-----|-----|--------|
| NSL2 | 65   | 61   | 64   | 64   | 62   | 63   | 62   | 60   | 56  | 54  | 59  | 58  | 52  | 53  | 45  | 44  | 23  | 23  | 42     |
| NSL1 |      | 61   | 65   | 63   | 64   | 63   | 61   | 63   | 58  | 54  | 56  | 55  | 53  | 52  | 46  | 46  | 29  | 25  | 41     |
| NCP1 |      |      | 69   | 81   | 78   | 67   | 65   | 65   | 60  | 57  | 53  | 54  | 50  | 53  | 44  | 45  | 25  | 25  | 41     |
| NCP2 |      |      |      | 69   | 72   | 91   | 70   | 72   | 63  | 62  | 57  | 58  | 53  | 55  | 43  | 44  | 30  | 27  | 40     |
| LCP1 |      |      |      |      | 75   | 67   | 67   | 66   | 59  | 59  | 52  | 52  | 51  | 54  | 42  | 42  | 24  | 26  | 42     |
| LCP2 |      |      |      |      |      | 70   | 70   | 68   | 61  | 57  | 56  | 55  | 52  | 54  | 45  | 44  | 26  | 23  | 41     |
| LCP3 |      |      |      |      |      |      | 68   | 69   | 63  | 61  | 60  | 56  | 53  | 53  | 44  | 44  | 30  | 26  | 38     |
| PCP1 |      |      |      |      |      |      |      | 89   | 62  | 59  | 60  | 56  | 53  | 55  | 47  | 46  | 23  | 26  | 38     |
| PCP2 |      |      |      |      |      |      |      |      | 64  | 61  | 55  | 57  | 56  | 57  | 48  | 48  | 24  | 27  | 39     |
| RCL  |      |      |      |      |      |      |      |      |     | 78  | 56  | 57  | 56  | 56  | 47  | 44  | 26  | 26  | 42     |
| HCL  |      |      |      |      |      |      |      |      |     |     | 59  | 56  | 58  | 60  | 45  | 43  | 28  | 28  | 38     |
| RCS  |      |      |      |      |      |      |      |      |     |     |     | 81  | 56  | 57  | 44  | 44  | 27  | 26  | 37     |
| HCS  |      |      |      |      |      |      |      |      |     |     |     |     | 57  | 58  | 44  | 45  | 28  | 28  | 40     |
| RCK  |      |      |      |      |      |      |      |      |     |     |     |     |     | 88  | 47  | 47  | 23  | 25  | 42     |
| HCK  |      |      |      |      |      |      |      |      |     |     |     |     |     |     | 48  | 49  | 24  | 26  | 43     |
| HCH  |      |      |      |      |      |      |      |      |     |     |     |     |     |     |     | 84  | 28  | 28  | 41     |
| RCH  |      |      |      |      |      |      |      |      |     |     |     |     |     |     |     |     | 27  | 28  | 37     |
| HCB  |      |      |      |      |      |      |      |      |     |     |     |     |     |     |     |     |     | 83  | 30     |
| RCB  |      |      |      |      |      |      |      |      |     |     |     |     |     |     |     |     |     |     | 27     |

Fig. 10
Coomassie staining
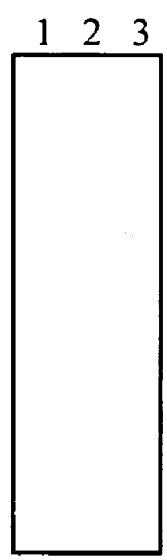
PAS staining
← Transferrin
← North shrimp cathepsin Fig. 13
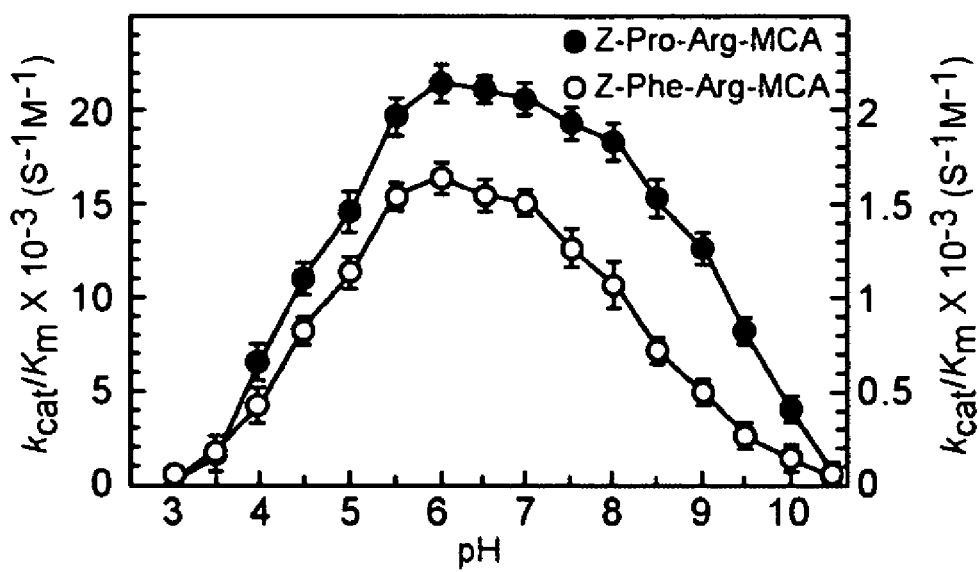
A.
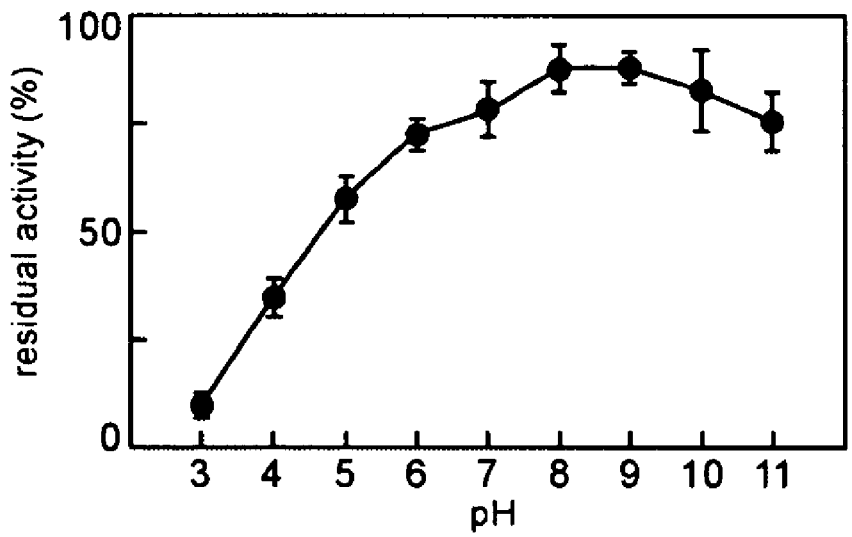
B.

CATHEPSINS L-LIKE CYSTEINE PROTEASE DERIVED FROM NORTHERN SHRIMP (*PANDALUS EOUS*)

This application is a continuation of Application No. PCT/JP03/07661 having an international filing date of Jun. 17, 2003, which designated the United States of America. This application also claims priority under 35 U.S.C. § 119(a) to Japanese Patent Application No. 2002-175773 filed Jun. 17, 2002, and also claims domestic priority under 35 U.S.C. § 119(e) to U.S. Provisional Application No. 60/471,733 filed May 20, 2003. The entire contents of all of the above-identified applications are hereby incorporated by reference.

BACKGROUND OF THE INVENTION

1. Field of the Invention

The present invention relates to novel cathepsin L-like enzyme extracted from northern shrimp (*Pandalus eous*), purification method thereof, polynucleotide encoding cathepsin L-like cysteine protease enzyme which is a novel protease newly identified from northern shrimp, polypeptide encoded by the same, and to the use of such polynucleotide and polypeptide.

2. Background Art

Protease is a generic term for enzymes that hydrolyze peptide bonds of proteins, and is widely spread among microorganisms, plants and animals. Numerous proteases having different catalyst groups and substrate specificity have been isolated. Their scope of application is also wide-ranging, and they are utilized, for example in modifiers of food products, detergents, cosmetic materials, clarifying agents for beer, tanning agents for leather, and medicaments.

Protease is one of the most important groups of enzymes which hydrolyze peptide bonds of protein, is widely spread among microorganisms, plants and animals, and is involved in various biological processes. In addition, proteases are categorized mainly into 4 families based on the catalyst groups: aspartic protease, cysteine protease, serine protease, and metalloprotease. The molecular action mechanism of these enzymes has been broadly investigated. SH protease (cysteine protease) having a SH group as active center includes enzymes such as bromelain. Cathepsins belonging to the papain superfamily of this cysteine protease are categorized into cathepsin L subfamily and cathepsin B subfamily. Cathepsin L subfamily includes cathepsins H, L, S, F, V, and W, and has 2 important motifs, i.e. ER(F/W)NIN motif and GNFD motifs which are dispersed motifs. The former ER(F/W)NIN motif does not exist in cathepsin B family and cathepsins C, O, and X.

In mammals, cathepsin L exists in lysosome and has potent endoprotease activity, although it has the characteristic that it does not show exo-type activity. Cathepsin L and cathepsin L-like cysteine proteases have so far been identified from several animals, and their sequences have been determined. These are listed below.

*Bombyx mori* (domestic silkworm)
Yamamoto Y., Takimoto K., Izumi S., Toriyama-Sakurai M., Kageyama T., Takahashi S. Y. Molecular cloning and sequencing of cDNA that encodes cysteine proteinase in the eggs of the silkmoth, *Bombyx mori*. J. Biochem. 116 (6):1330-1335(1994).

*Bos taurus* (cow)
Unpublished.

*Drosophila melanogaster* (fruit fly)
Tryselius Y., Hultmark D. Cysteine proteinase 1 (CP1), a cathepsin L-like enzyme expressed in the *Drosophila melanogaster* haemocyte cell line mbn-2. Insect Mol. Biol. 6(2): 173-181(1997).

*Homo sapiens* (human)
Joseph L. J., Chang L. C., Stamenkovich D., Sukhatme V. P. Complete nucleotide and deduced amino acid sequences of human and murine preprocathepsin L. An abundant transcript induced by transformation of fibroblasts. J. Clin. Invest. 81(5):1621-1629(1988).

*Homarus americanus* (American lobster)
Laycock M. V., MacKay R. M., Di Fruscio M., Gallant J. W. Molecular cloning of three cDNAs that encode cysteine proteinases in the digestive gland of the American lobster (*Homarus americanus*). FEBS Lett. 292:115-120(1991).

*Mus musculus* (Mouse)
Portnoy D. A., Erickson A. H., Kochan J., Ravetch J. V., Unkeless J. C. Cloning and characterization of a mouse cysteine proteinase. J. Biol. Chem. 261:14697-14703 (1986).

*Nephrops norvegicus* (Norway lobster)
Le Boulay C., Van Wormhoudt A., Sellos D. Molecular cloning and sequencing of two cDNAs encoding cathepsin L-related cysteine proteinases in the nervous system and in the stomach of the Norway lobster (*Nephrops norvegicus*). Comp. Biochem. Physiol. 111:353-359(1995).

*Penaeus vannamei* (Pacific white shrimp)
Le Boulay C., Van Wormhoudt A., Sellos D. Cloning and expression of cathepsin L-like proteinases in the hepatopancreas of the shrimp *Penaeus vannamei* during the intermoltcycle. J. Comp. Physiol. B 166:310-318(1996).

*Rattus norvegicus* (Norway rat)
Ishidoh K., Towatari T., Imajoh S., Kawasaki H., Kominami E., Katunuma N. Suzuki K. Molecular clonig and sequencing of cDNA for rat cathepsin L. FEBS Lett. 223:69-73 (1987).

With respect to collagenolytic activity of cathepsin L, it has been reported that cathepsin L of rat degrades collagen under acidic conditions at 37° C. Barrett, A. J. and Kirschke, H., Cathepsin B, Cathepsin H, and Cathepsin L., Methods Enzymol. 80, 535-561. (1981).

SUMMARY OF THE INVENTION

The cathepsin L described above has optimal pH under acidic condition and optimal temperature of 50 to 70° C. Among those reported in the above document, some have done only gene cloning of the enzyme, thus their identities and properties have not been investigated. Either way, cathepsin L having high activity under neutral to alkaline conditions at a low temperature has not been known until now. If cathepsin L having high activity even under neutral to alkaline conditions and at a low temperature was found, it enables to modifiy the properties of protein material will be enabled while avoiding deterioration of properties due to protein denaturing, and to provide enzymes greatly useful in application to modifiers of food products, detergents, cosmetic materials, and medicaments.

The present inventors looked for proteases in the natural environment which degrade collagen even at a low temperature. As a result of numerous extensive screenings, the present inventors unexpectedly succeeded in finding a novel protease having activity even at a low temperature in hepatopancreas of Japanese northern shrimp. The protease of the present invention is cathepsin L-like cysteine protease.

Northern shrimp is a cold-adapted aquatic organism typically inhabiting at a low temperature environment of −1.6 to 5° C., and is spread across the North Pacific and the North Atlantic Oceans. Several reports show that enzymes of cold-adapted species exhibit substantially higher catalytic efficiency than their corresponding enzymes of mammals. For example, in the case of serine protease trypsin, which is one of the most researched proteases, it is reported that the catalytic efficiency of salmon trypsin is 40 times higher compared to bovine trypsin.

For screening, the present inventors prevented the hepatopancreatic cells from being destructed from freezing by removing hepatopancreas from raw, unfrozen northern shrimp. It was devised so that enzymes in hepatopancreatic cells were extracted without being degraded. The present inventors also discovered a way to purify the cathepsin L-like cysteine protease of the present invention from deep-frozen hepatopancreas.

The cathepsin L-like protein of the present invention can be purified from northern shrimp by appropriate combination of ion exchange column, gel filtration column, adsorption column, salt precipitation, dialysis, ultrafiltration, centrifugation, etc. For example, hepatopancreas is excised from raw northern shrimp, homogenized, delipidated, and then the protein is precipitated by ammonium sulfate and redissolved. The supernatant is purified by anion exchange column, separated by adsorption chromatography, and repurified by ion exchange chromatography to prepare the protein. Anion exchange chromatography which can be used include, for example, Q-Sepharose and Mono Q; and adsorption chromatography which can be used include, for example, hydroxyapatite. Similarly, preparation can also be carried out using hepatopancreas of thawed northern shrimp, by homogenation, delipidation, followed by centrifugation and precipitation of the protein, redissolving, dialysis, and finally purification of dialysate by anion exchange column, separation by gel filtration chromatography, and purification by adsorption chromatography. Anion exchange chromatography which can be used include, for example, Q-Sepharose and Mono Q; gel filtration chromatography which can be used include, for example, Superdex; and adsorption chromatography which can be used include, for example, hydroxyapatite.

The cathepsin L-like cysteine protease of northern shrimp thus obtained was shown to (1) have molecular weight of approximately 30 KDa, (2) have optimal pH of approximately 7 to 8, (3) have optimal temperature of approximately 35° C., (4) show collagenolytic activity, and (5) show cathepsin L-like activity. In addition, as a result of various investigations utilizing genetic engineering approaches, the present inventors have succeeded in cloning the gene encoding this enzyme, and in revealing complete base sequence of the gene and deducted amino acid sequence, thus leading to the completion of the invention. The present inventors have also succeeded in cloning genes encoding isoforms predicted to have similar conformational structure as the enzyme of the present invention, and revealed their properties by expressing them in an expression system using yeasts.

Isoforms of the expressed cathepsin L-like cysteine protease of northern shrimp (1) have molecular weight of approximately 30 KDa, (2) have optimal pH of approximately 6 to 8, (3) have optimal temperature of approximately 40° C. (activity was exhibited even at 20° C.), (4) show collagenolytic activity, and (5) show cathepsin L-like activity.

These novel cathepsin L-like cysteine proteases derived from northern shrimp are each designated northern shrimp cathepsin L1 and northern shrimp cathepsin L2. In addition, northern shrimp cathepsin L1 is sometimes also called NSL1 or NsCtL, and northern shrimp cathepsin L2 is sometimes also called northern shrimp cysteine protease, NsCys, or Crustapain.

Northern shrimp cathepsins L1 or L2 can be produced by genetic recombination wherein gene encoding northern shrimp cathepsins L1 or L2 is integrated into appropriate expression vectors, and then introducing said recombinant expression vectors into appropriate hosts. Various known vectors can be used as expression vectors. Examples of vectors when using E. coli as host include series of pUR vectors, pATH vectors, and pGEX vectors. Vectors such as pXM and pDC 201 can be used when using animal cells such as COS and CHO as hosts.

In a system using E. coli., for example, the genes of the present invention are inserted into expression vectors pGEX (Amersham Pharmacia), pET39b (Novagen), and pRSET (Invitrogen), introduced into E. coli, to induce expression. The expression of genes having the intended molecular weight was confirmed by SDS-PAGE. In a system utilizing yeasts, yeast expression vector pPICZα into which gene of present was inserted was introduced into host yeast P. pastoris X-33 strain or KM71H strain by electroporation, and transformants able to grow in a medium containing high concentration (2000 μg/ml) of zeocin were selected. Activity was verified by gelatin zymography and bands of the size corresponding to the intended enzyme were detected.

The present invention encompasses the two isolated cathepsin L-like proteases described above and naturally occurring variants thereof. The present invention further encompasses proteins consisting of amino acid sequences having deletion, substitution or addition of one or more amino acids in the amino acid sequences of northern shrimp cathepsins L1 or L2, and having cathepsin L-like enzyme activity. The present invention also encompasses the preproenzymes of these cathepsin L-like enzymes. The present invention also encompasses polypeptides wherein the polypeptides are 80% or more identical to all or a portion of the amino acid sequences of these cathepsins L1 or L2. The present invention additionally encompasses signal peptides and propeptides of these cathepsin L-like enzymes. These propeptides are also useful as inhibitors of the present cathepsin-like enzymes. In addition, the present invention encompasses DNA encoding these enzymes, signal peptides thereof, and the propeptides.

The present invention for example encompasses DNA encoding proteins which hybridize under stringent conditions to DNA consisting of the complementary strand of the above northern shrimp cathepsin L1, northern shrimp cathepsin L2, or their respective preproenzymes, and which have cathepsin L-like enzyme activity.

Hybridization under stringent conditions means to start with prehybridization by treating Hybond N+ nylon membranes (Amersham Pharmacia) on which DNA is attached by treatment at 120° C. for 20 minutes, in Church phosphate buffer (0.5 M $Na_2HPO_4$, 1 mM EDTA, 7% SDS) at 65° C. for 5 minutes. Hybridization is performed in the same buffer by adding the probes obtained by the process described below at 65° C. for 17 hours. The hybridized membrane is treated at room temperature for 20 minutes in 2×SSC (standard saline citrate; 1×SSC is 150 mM NaCl, 15 mM sodium citrate, pH 7.0) containing 0.1% SDS, and then washed twice with 1×SSC containing 0.1% SDS at 65° C. for 20 minutes each. The membrane is additionally treated with 0.1×SSC containing 0.1% SDS at 65° C. for 20 minutes to complete the washing. Exposure to X-ray films is carried out at −80° C. for 24 hours.

In preparing probes, for example, cDNA fragments amplified by PCR are labeled with [$\alpha^{32}P$]-dCTP using Takara random primer DNA labeling kit Ver. 2 (Takara). Unreacted isotopes are then removed using centrifugation filters (Millipore).

The present invention further encompasses DNA encoding northern shrimp cathepsin L1, northern shrimp cathepsin L2, or proteins consisting of amino acid sequences containing deletion, substitution or addition of one or more amino acids in the amino acid sequences of preproenzymes thereof and having cathepsin L-like enzyme activity, or DNA encoding preproenzymes having cathepsin L-like enzyme activity.

The present invention also encompasses DNA in which 1 to 100, preferably 1 to 10, more preferably 1 to several bases are deleted, substituted or added in the DNA encoding northern shrimp cathepsin L1, northern shrimp cathepsin L2, or preproenzymes thereof, wherein the DNA encodes proteins having the activity of northern shrimp cathepsins L1 or L2.

The present invention also encompasses DNA having the ability to produce polypeptides which are 80% or more, preferably 90% or more, most preferably 95% or more identical to all or a portion of the amino acid sequences of northern shrimp cathepsins L1 or L2. The present invention further encompasses DNA of which homology to DNA sequences encoding cathepsin L or prepro-cathepsin L is 80% or more, preferably 90% or more, most preferably 95% or more, and encoding proteins having cathepsin L-like enzyme activity or functioning as prepro-cathepsin L-like enzyme.

The present invention encompasses primers for detecting these genes, for example a sequence of 15 or more consecutive bases within the base sequences of L1 or L2, or a base sequence in which 1 or more bases are deleted, substituted, or added from or to the said sequence.

The S2 pocket of the northern shrimp cathepsins L1 or L2 of the present invention is mainly hydrophobic, and is composed of amino acids 67, 68, 157, 160, and 205 with respect to the amino acid sequence of mature papain(in accord with the numbering representation in Schechter, I. and Berger, A. (1967) On the size of the active site in proteinases, I. Papain. Biochem. Biophys. Res. Commun. 27, 157-162). In the case of northern shrimp cathepsin L1, amino acids 67 and 68 are Val, 133 is Cys, 157 is Ile, 160 is Ala, and 205 is Gln in the amino acid sequence of mature papain. In the case of northern shrimp cathepsin L2, amino acid 67 is Trp, 68 is Pro, 133 is Cys, 157 is Ala, 160 is Ala, and 205 is Tyr in the amino acid sequence of the same.

The present invention encompasses proteins composed of amino acid sequences in which deletion, substitution or addition of one or more amino acids from the amino acid sequences of northern shrimp cathepsins L1 or L2, and having cathepsin L-like enzyme activity which has the same substrate specificity as northern shrimp cathepsins L1 or L2. The said proteins are characterized in that (1) amino acids 67 and 68 are Val, 133 is Cys, 157 is Ile, 160 is Ala, and 205 is Gln, or (2) amino acid 67 is Trp, 68 is Pro, 133 is Cys, 157 is Ala, 160 is Ala, and 205 is Tyr in the amino acid sequence of mature papain, so as to retain the S2 pocket of northern shrimp cathepsins L1 or L2.

BRIEF DESCRIPTION OF THE DRAWINGS

FIG. 1 shows base sequence and deduced amino acid sequence of northern shrimp cathepsin L1;

FIG. 2 shows base sequence and deduced amino acid sequence of northern shrimp cathepsin L2;

Figure 4:
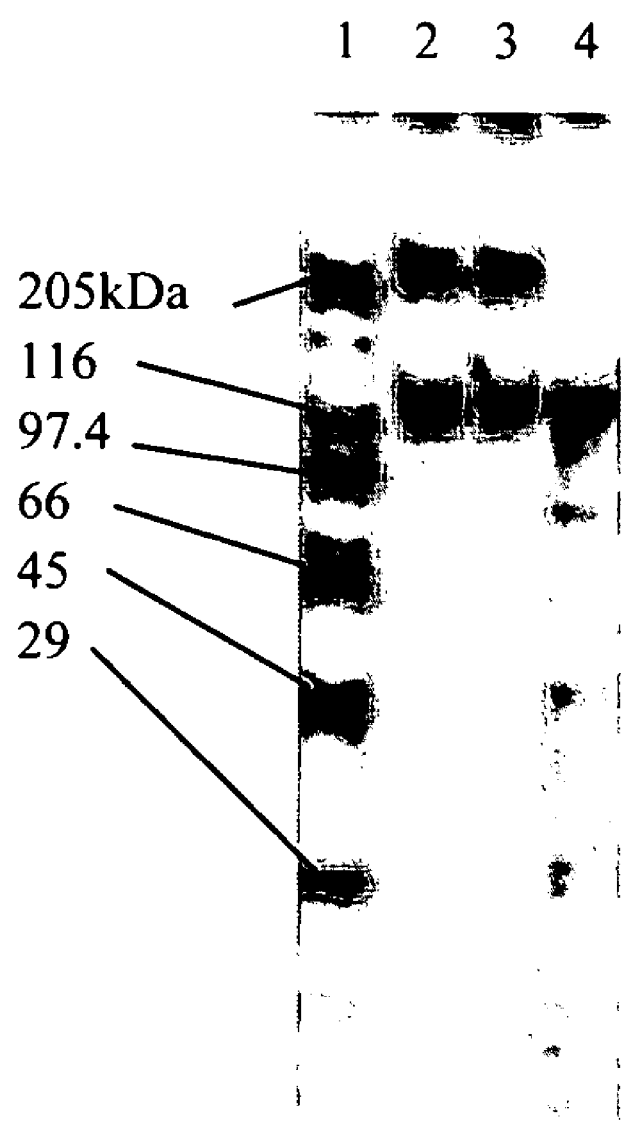
Figure 5:
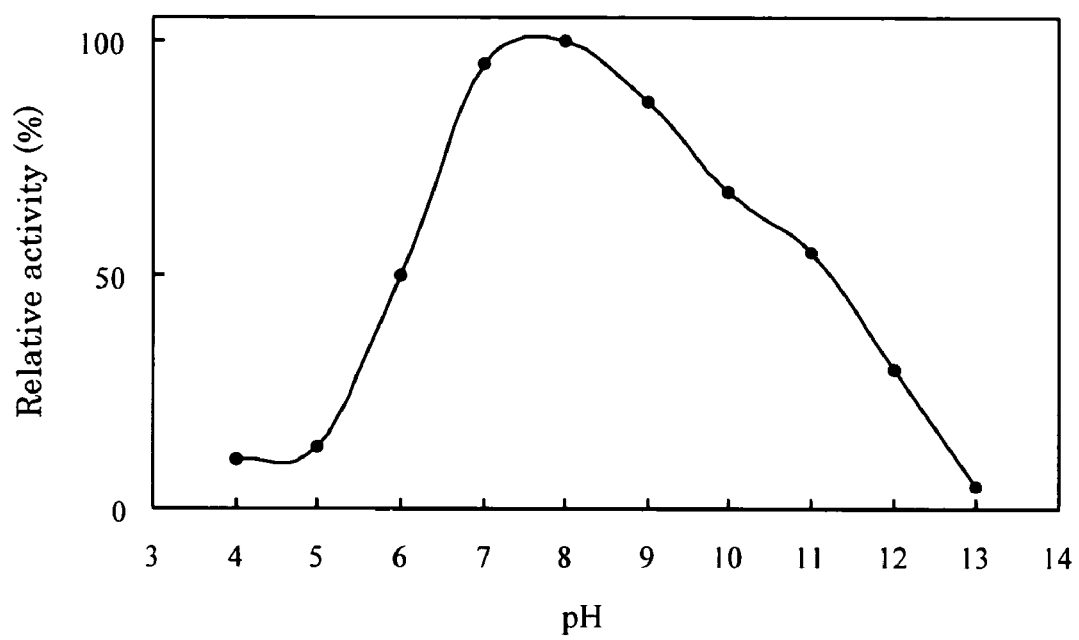
Figure 6:
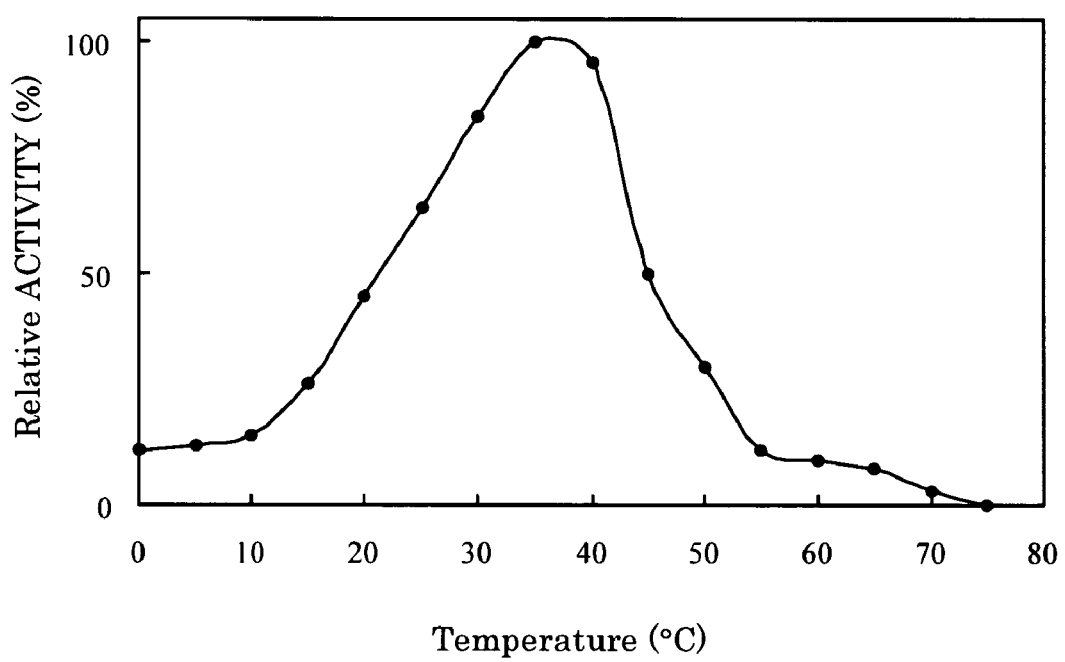
Figure 7:
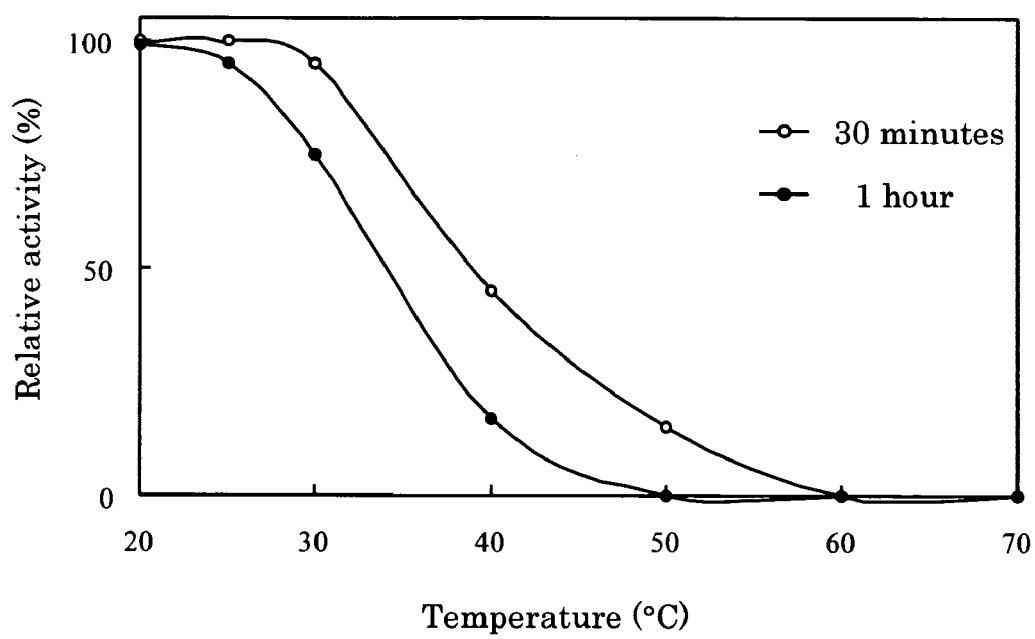
Figure 9A:
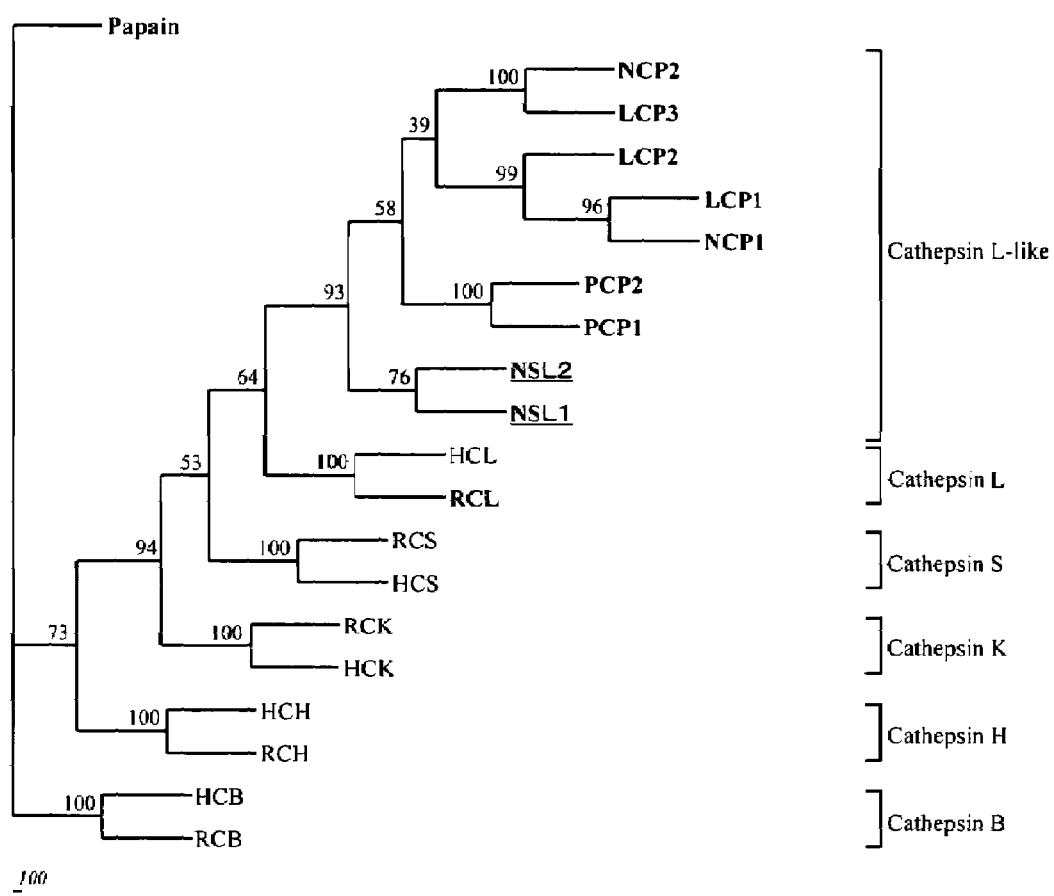

Lane 1: molecular weight markers, Lane 2: northern shrimp cathepsin L1 (10 µg);

FIG. 4 shows the pattern of collagenolysis by northern shrimp cathepsin L1:

Lane 1: molecular weight markers, Lane 2: collagen, Lane 3: no reaction, Lane 4: reaction at 25° C., 30 minutes;

FIG. 5 shows the optimal pH of northern shrimp cathepsin L1;

FIG. 6 shows the optimal temperature of northern shrimp cathepsin L1;

FIG. 7 shows the thermal stability of northern shrimp cathepsin L1;

FIG. 8 shows the sequence comparison between amino acid sequences of northern shrimp cathepsins L1 and L2, and cathepsin L of other crustacean and rat cathepsin L and papain:

Position numbers are based on the position number of papain. Identical residues are represented by dots, and gaps are inserted to achieve maximum match. Cysteines forming the three S—S bonds are shown in gray, and the active centers Cys, His, and Asp are reverse printed. Northern shrimp cathepsins L1 and L2 each correspond to Northern Shrimp 1 and 2;

FIG. 9 shows (A) the phylogenetic tree of cathepsins belonging to papain super family and (B) homology between the amino acid sequences:

The phylogenetic tree was constructed by neighbor-joining method based on parallel alignment of the sequences of mature enzymes. Sequences appearing in FIG. 8 are shown in bold. Numbers at branching points represent bootstrap values (%). Northern shrimp cathepsin L-like cysteine proteases L1 and L2 (each abbreviated NSL1 and NSL2) are compared with papain, rat cathepsins B, H, K, S, and L (each abbreviated RCB, RCH, RCK, RCS, and RCL), American lobster (*Homarus america*) cysteine proteases 1, 2, and 3 (each abbreviated LCP1, LCP2, and LCP3), cathepsin L in the nervous system and in the stomach of Norway lobster (*Nephros norvegicus*) (each abbreviated NCP1 and NCP2), and cathepsins L1 and L2 of white shrimp (*Penaeus vannamei*) (each abbreviated PCP1 and PCP2);

FIG. 10 shows PAS (periodic acid Schiff) staining of northern shrimp cathepsin L1 in acrylamide:

Lane 1: molecular weight markers

Lane 2: northern shrimp cathepsin L1 (10 µg)

Figure 12:
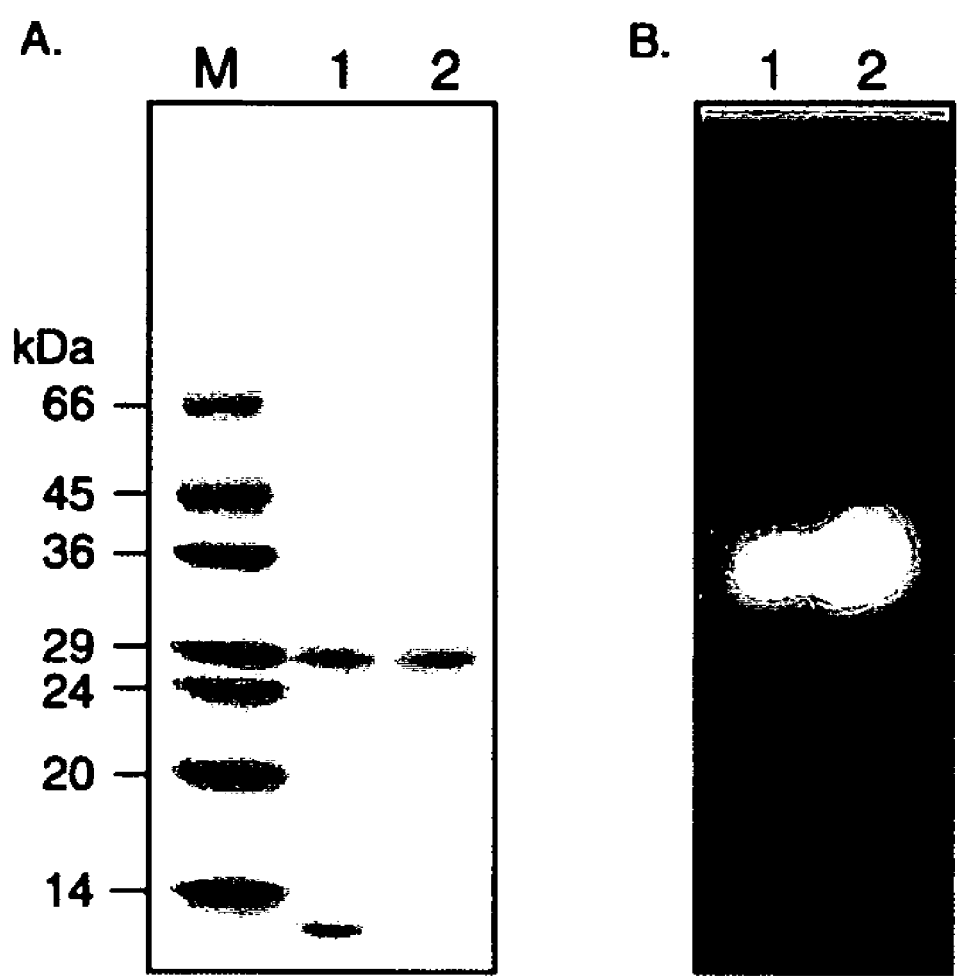

Lane 3: transferrin (10 µg);

FIG. 11:

"Assay for substrate specificity of northern shrimp cathepsin L1 using fluorescent substrates of di- or tri-peptides. Di- or tri-peptidic fluorescent MCA substrates represented by Z-Xaa-Xaa-Arg-MCA (Xaa represents a different amino acid which can be represented by a 1-letter amino acid notation) were used.":

In the Figure, FR represents Z-Phe-Arg-MCA, RR represents Z-Arg-Arg-MCA, PR represents Z-Pro-Arg-MCA, VVR represents Z-Val-Val-Arg-MCA, LLR represents Z-Leu-Leu-Arg-MCA, and FVR represents Z-Phe-Val-Arg-MCA;

FIG. 12 shows SDS-PAGE (FIG. 12A) and gelatin zymography (FIG. 12B) of northern shrimp cathepsin L2 produced by a yeast expression system:

Lane 1 shows propeptides containing northern shrimp cathepsin L2 (NsCys), and Lane 2 shows mature northern shrimp cathepsin L2 (NsCys);

FIG. 13 shows the pH profile and pH stability of the activity of northern shrimp cathepsin L2:

A: With respect to hydrolysis of Z-Pro-Arg-MCA and Z-Phe-Arg-MCA measured under conditions of pseudo first-order reaction, pH-dependant second-order rate constant ($K_{cat}/K_m$) of northern shrimp cathepsin L (NsCys) is shown on the left and right axes, respectively.

Figure 14:
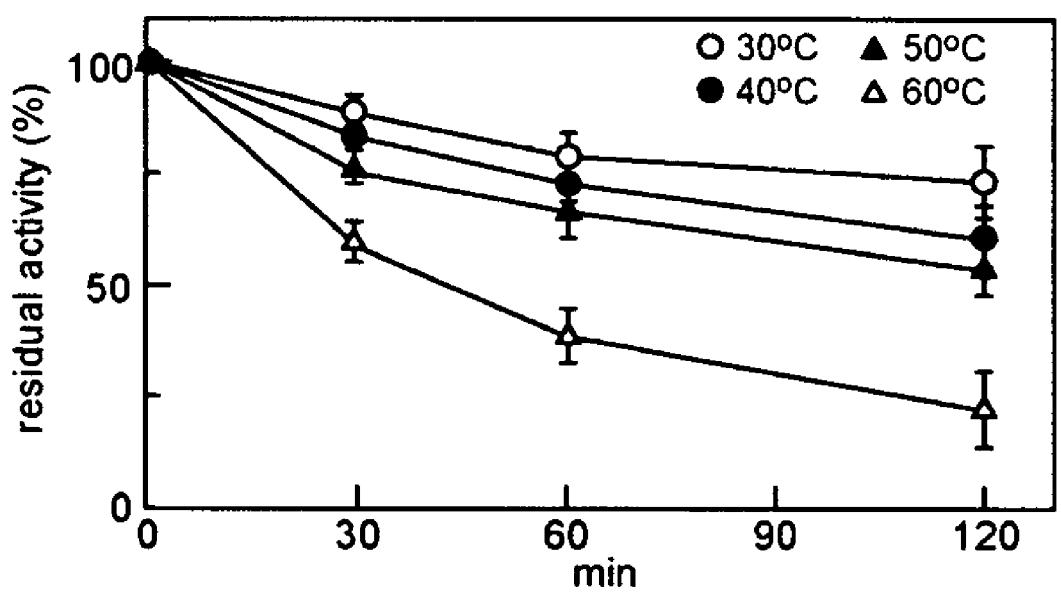
Figure 15:
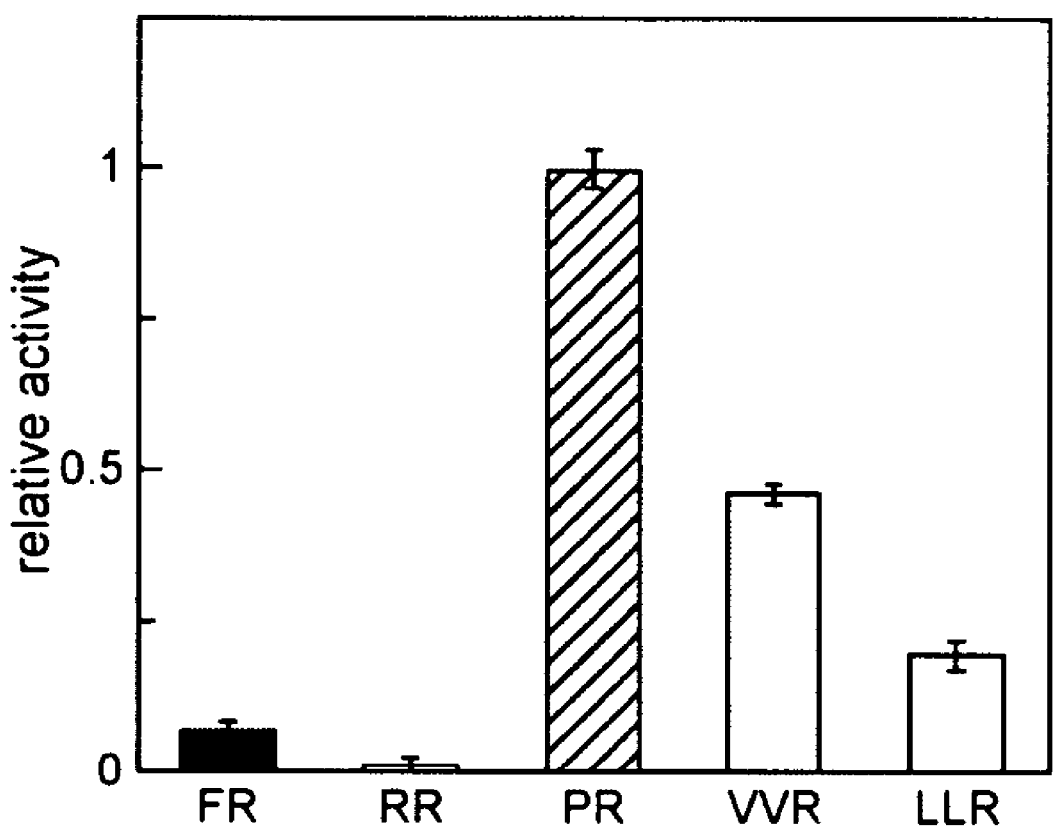

B: Residual activity towards Z-Pro-Arg-MCA at pH 6.0 after treatment for 30 minutes in buffers of various pH. Data at each pH is shown in percentage vs. untreated sample;

FIG. 14 shows the thermal stability of northern shrimp cathepsin L2;

FIG. 15 shows the substrate specificity of northern shrimp cathepsin L2;

Di- or tri-peptide fluorescent MCA substrates represented by Z-Xaa-Xaa-Arg-MCA (Xaa indicates a different amino acid which can be represented by a three-letter amino acid notation) were used.

Figure 16:
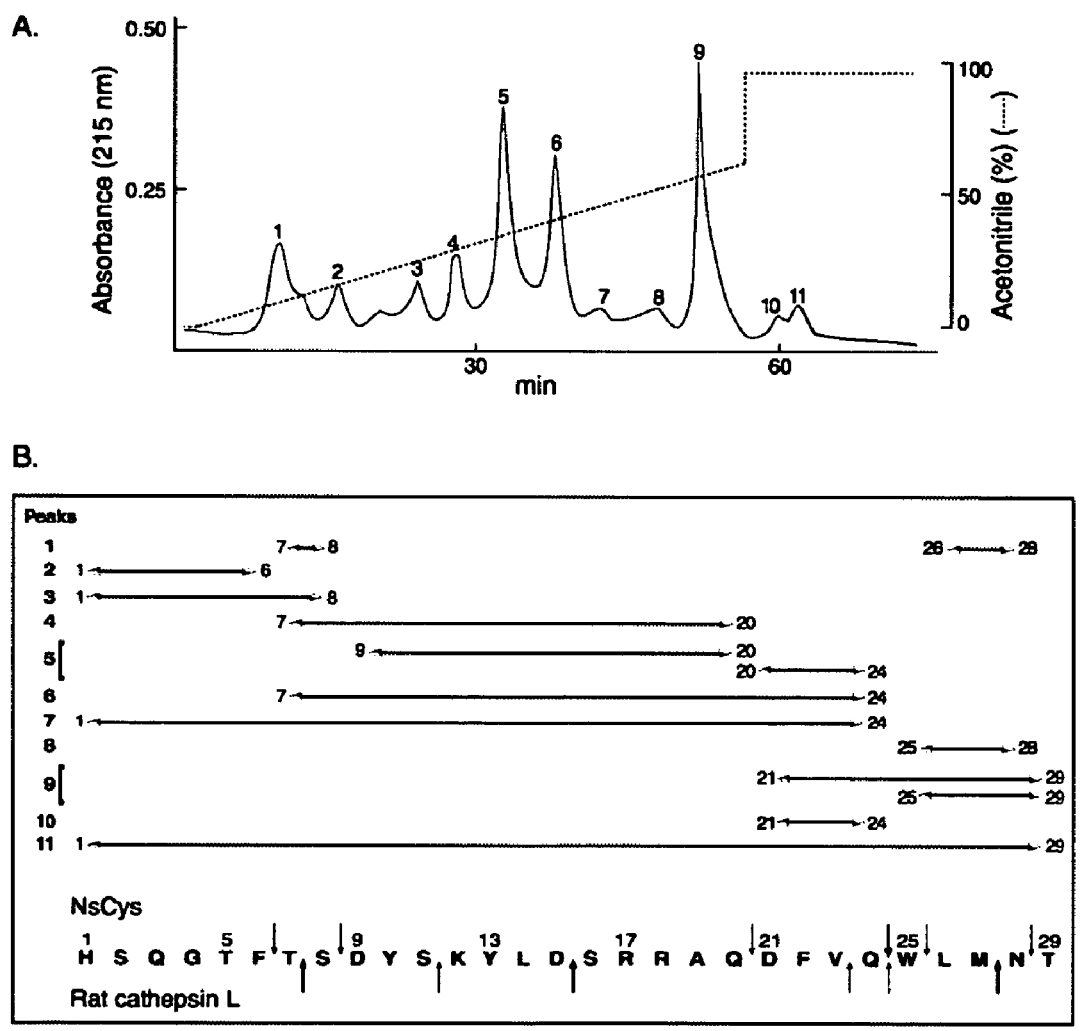

In FIG. 15, FR represents Z-Phe-Arg-MCA, RR represents Z-Arg-Arg-MCA, PR represents Z-Pro-Arg-MCA, VVR represents Z-Val-Val-Arg-MCA, and LLR represents Z-Leu-Leu-Arg-MCA;

FIG. 16 shows the degradation of glucagon by northern shrimp cathepsin L2:

A: Peaks showing the results of separation by reverse phase HPLC of fragments which are produced from glucagon degradation by northern shrimp cathepsin L2 (denoted by numbers)

B: amino acid sequences of fragments (peak numbers) separated by reverse phase HPLC were determined.

Amino acid sequence of glucagon is shown at the bottom. The sensitivity of each cleavage site is estimated from the height of peak of the chromatography. Major cleavage sites are shown with bold arrows, moderate cleavage sites are shown with narrow arrows, and minor cleavage sites are shown with broken lines, along with cleavage sites by rat cathepsin L.

Figure 17:
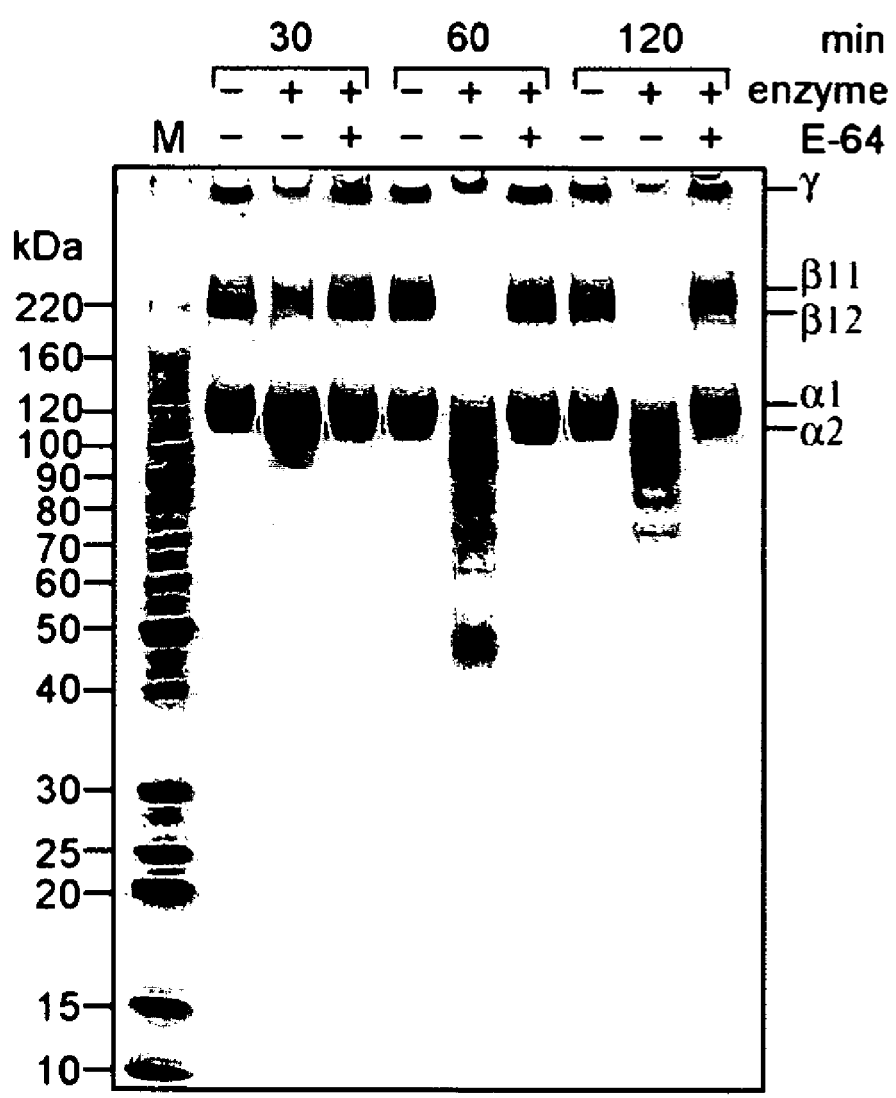

The difference in cleave sites compared to other cathepsin L is well indicated; and FIG. 17 is the SDS-PAGE showing the results of degradation of type I collagen by northern shrimp cathepsin L2.

DETAILED DESCRIPTION OF THE PREFERRED EMBODIMENTS

The Examples are for exemplification and do not limit the present invention.

EXAMPLE 1

Separation and Purification of Cathepsin L-like Enzymes from Northern Shrimp

<Purification of Northern Shrimp Cathepsin L1>

Live northern shrimps were bought from fishery cooperative society, and dissected to obtain hepatopancreases. Two volumes of 50 mM Tris-HCl (pH 7.5) was added to this hepatopancreas and homogenized. 1/5 volume of tetrachloromethane was then added, stirred at 4° C. for 1 hour for delipidation, and centrifugated (18,000 g, 4° C., 30 minutes). The obtained supernatant was subjected to ammonium sulfate fractionation. Precipitate with ammonium sulfate of 17.6 to 47.2% (w/v) was dissolved in 20 mM Tris-HCl (pH 7.5) containing 5 mM $CaCl_2$ and 0.02% $NaN_3$ (Buffer A), dialyzed, and then subjected to Q-Sepharose column (Amersham Pharmacia) equilibrated with Buffer A. The unattached fraction was washed with Buffer A, followed by elution with a linear gradient using Buffer A and Buffer A containing 0.6 M NaCl.

The active fraction was collected, dialyzed against 10 mM potassium phosphate buffer (pH 6.9), loaded onto hydroxyapatite (Bio-Rad) column equilibrated with the same buffer, and eluted with a linear gradient using the same buffer and 400 mM potassium phosphate buffer (pH 6.9). Further, the active fraction was subjected to Mono Q column. Elution was carried out with a linear gradient using Buffer A and Buffer A containing 1M NaCl. Northern shrimp cathepsin L1 was purified by the method described above. Relative activity of each purification step measured with synthesized substrate is shown in Tables 1 and 2.

<Method for Measuring Enzymatic Activity>

The collagenolytic activity of fractions from each purification step and of purified enzyme were confirmed by SDS-PAGE after a 30-minute reaction at pH 7.5 and at 25° C., using acid-soluble type I collagen (Wako Pure Chemical Industries, Ltd.) as substrates (FIG. 4).

In addition, the enzymatic activity in the course of purification was quantitatively monitored by a method using synthesized substrates as shown below.

DNP-Pro-Gln-Gly-Ile-Ala-Gly-Gln-D-Arg (Peptide Institute, Inc) (hereinafter referred to as DNP-peptide) was used as the substrate for measuring the activity of collagenase-like enzyme. Substrate solution was prepared by dissolving DNP-peptide at a concentration of 1 mM in 50 mM Tris-HCl buffer containing 150 mM NaCl (pH 7.5). Equal volume of enzyme solution from each fraction was added to 100 ml of the substrate solution and reacted at 25° C. for 10 minutes. The reaction was terminated by adding 0.5 ml of 1N HCl. A mixture of ethyl acetate and n-butanol (1:0.15) was added and shaked vigorously. Then, following centrifugation, absorbance of the supernatant was measured at 365 nm. One unit is defined as the amount of enzyme hydrolyzing 1 µmol of substrate per minute.

Substrates used for measuring the activities of trypsin-like enzyme and elastase-like enzyme included Bz-DL-Arg-pNA (BAPA), Suc-(Ala)3-pNA (STANA)(Peptide Institute, Inc), Suc-Ala-Ala-Pro-Arg-pNA (AAPR), and Suc-Ala-Ala-Pro-Leu-pNA (AAPL) (BACHEM) (Bz represents Benzoyl, pNA represents p-Nitroanilide, and Suc represents Succinyl). The presence of trypsin-like enzyme activity can be determined by degradation of BAPA, and the presence of elastase-like enzyme activity can be determined by degradation of STANA. AAPL and AAPR are substrates which serine collagenase derived from crab acts upon. Substrate solution at a concentration of 50 mM was prepared with dimethyl sulfoxide. Enzyme solution from each fraction was added to 50 mM Tris-HCl buffer containing 150 mM NaCl (pH 7.5) and pre-incubated, and then the substrate solution was added at a final concentration of 0.5 mM, reacted at 25° C. for 5 minutes, and colorimetric determination of the released p-nitoraniline was performed at 405 nm. One unit is defined as the amount of enzyme hydrolyzing 1 µmol of substrate per minute.

The amount of protein in each fraction was quantified by Bradford method using BSA as a standard.

TABLE 1

Relative activity in each purification step assayed using DNP-Peptide

| Step | Total protein (mg) | Total activity (U) | Relative activity (U/mg) | Degree of purification (fold) | Yield (%) |
| --- | --- | --- | --- | --- | --- |
| Ammonium sulfate precipitation | 916 | 30.605 | 0.033 | 1 | 100 |
| Q-Sepharose FF | 31.7 | 7.892 | 0.249 | 7.4 | 25.8 |
| Hydroxyapatite | 1.16 | 2.562 | 2.213 | 66.2 | 8.37 |
| MonoQ | 0.153 | 1.521 | 9.944 | 297.5 | 4.97 |

TABLE 2

| Step | Relative activity (U/mg) | | | |
|---|---|---|---|---|
| | AAPL | AAPR | BAPA | STANA |
| Ammonium sulfate precipitation | 0.169 | 0.068 | 0.006 | 0.018 |
| Q-Sepharose FF | 0.351 | 0.112 | 0.002 | 0.020 |
| Hydroxyapatite | 2.548 | 0.722 | 0.000 | 0.106 |
| MonoQ | 12.094 | 2.441 | 0.000 | 0.182 |

Purified northern shrimp cathepsin L1 worked well towards synthesized substrates of collagenase (Table 1). It did not work at all towards BAPA, and worked well towards substrates having proline at P2 position (AAPL, AAPR) (Table 2).

Activity was further measured using Z-Phe-Arg-MCA as the substrate for determining cathepsin L-like activity. Substrate solution at a concentration of 20 mM was prepared with dimethyl sulfoxide. Enzyme solution was added to 50 mM Tris-HCl buffer containing 150 mM NaCl (pH 7.5) and pre-incubated, and then the substrate solution was added at a final concentration of 50 μM. Reaction at 25° C. was carried out for 5 minutes, and fluorescence intensity of the released 7-amino-4-methylcoumarin (AMC) was measured at an excitation wavelength of 380 nm and an emission wavelength of 460 nm. Calibration curve was prepared using AMC (Peptide Institute, Inc) and quantified. One U is defined as the amount of enzyme hydrolyzing 1 μmol of substrate per minute. Activity of 10.2 U/mg was observed at the final step of purification.

Collagenolytic pattern by northern shrimp cathepsin L1 is shown in FIG. 4. As shown in the figure, the present enzyme degrades collagen well in a reaction of 30 minutes at 25° C.

Figure 3:
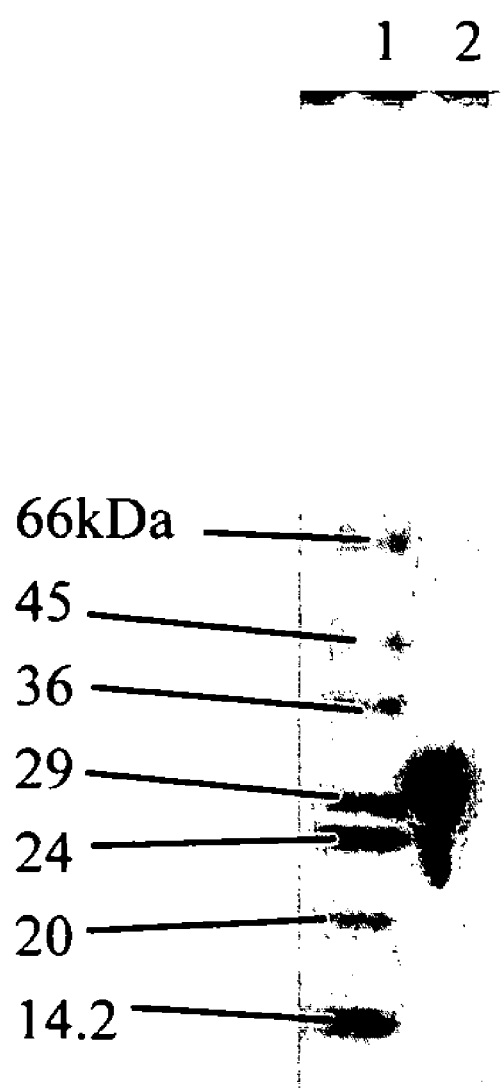
FIG. 3 shows the SDS-PAGE of northern shrimp cathepsin L1.

SDS-PAGE pattern of northern shrimp cathepsin L1 is shown in FIG. 3. The cathepsin was obtained as a single band around approximately 30 kDa.

PAS staining was carried out as follows.

The gel from SDS-PAGE was soaked in 12.5% trichloroacetic acid for 30 minutes, washed with distilled water for 30 seconds, soaked in 0.5% periodic acid solution (for PAS staining) (Wako Pure Chemical Industries, Ltd.) for 50 minutes, washed well with distilled water for 10 minutes×6 times, treated with Cold Schiff's Reagent (Wako Pure Chemical Industries, Ltd.) for 50 minutes, washed with 0.05 NHCl containing 0.5% sodium bisulfite for 10 minutes×3 times, washed with distilled water, and then soaked in 5% acetic acid. The results suggested that northern shrimp cathepsin L1 has carbohydrate chains (FIG. 10).

<Optimal pH>

Measurement of activity was carried out at 25° C. in Britton-Robinson buffer (pH 4 to 13) using DNP-peptide. The final reacting solution was 200 μl, and the final concentrations of DNP-peptide and enzyme were 0.5 mM and 1.5 μg/ml, respectively. The optimal pH of the present enzyme was approximately 7 to 8 (FIG. 5).

<Optimal Temperature>

One mM DNP-peptide and 50 mM Tris-HCl buffer containing 150 mM NaCl (pH 7.5) were preincubated at different temperatures for 5 minutes, and then the enzyme was added to measure activity. The final reacting solution was 200 μl, and the final concentrations of DNP-peptide and enzyme were 0.5 mM and 1.5 μg/ml, respectively. The optimal temperature of the present enzyme was approximately 35° C. (FIG. 6).

<Thermal Stability>

The present enzyme (300 ng) was added to 50 mM Tris-HCl buffer containing 150 mM NaCl (pH 7.5), incubated at different temperatures (20° C. to 70° C.) for 30 minutes and 60 minutes, and then immediately cooled on ice. Residual activity was measured at 25° C. using DNP-peptide as the substrate. The final reacting solution was 200 μl, and the final concentrations of DNP-peptide and enzyme were 0.5 mM and 1.5 μg/ml, respectively. The present enzyme was stable up to incubations at 25° C. for 1 hour and at 30° C. for 30 minutes, and was inactivated by incubations at 50° C. for 1 hour and at 60° C. for 30 minutes (FIG. 7).

EXAMPLE 2

<Analysis of N-Terminal Amino Acid Sequence>

Purified northern shrimp cathepsin L1 was subjected to electrophoresis, and then transferred from the SDS polyacrylamide gel to PVDF membrane. The corresponding band was excised and was subjected to protein sequencing. The N-terminal amino acid sequence of the present enzyme was DTVDWRDKGAVTPVKDQGQ. As a result of homology search, this corresponded to the N-terminal vicinity of active cysteine protease.

EXAMPLE 3

<Cloning of Cathepsin L>

Oligonucleotides were prepared with reference to a portion of the determined N-terminal amino acid sequence, DWRDKGA. The prepared primers were 5'-GAY TGG CGN GAY AAR GGN GC-3' (R: A/G, Y: C/T, N: A/G/C/T).

Total RNA was prepared from hepatopancreas of northern shrimp using ISOGEN (Nippon Gene Co., Ltd.). Single stranded cDNA was then synthesized by 3' RACE System (GIBCO BRL). The single stranded cDNA was used as a template to carry out PCR (30 cycles; 94° C. for 30 seconds, 55° C. for 30 seconds, 72° C. for 1 minute) using the primers described above and AUAP of the 3' RACE System. PCR products of approximately 900 bp were obtained. These fragments were inserted into pGEM-T Easy Vector (Promega), subcloned, and the base sequence at 3'-terminus was determined. As a result, 2 types of sequences were obtained, and primers for antisense strands as shown in Table 3 were prepared based on these sequences. PCR fragments obtained with 5' RACE System (GIBCO BRL) were similarly subcloned, and the base sequence at 5'-terminus was determined.

TABLE 3

Primers used for 5' RACE

| | Nucleotide sequence |
|---|---|
| L1-R1 | 5'-GCA TCA ATA CAG ACG CTG AC-3' |
| L1-R2 | 5'-CAT CAG CAT AAG GGA TAT CTG-3' |
| L1-R3 | 5'-AAC GTG TGC AGC GTC GAA TC-3' |
| L2-R1 | 5'-GTC TCA TCT CCT TCG GTT AC-3' |
| L2-R2 | 5'-ACC TTG AAT GGT GGC ACC GA-3' |
| L2-R3 | 5'-CGC ACT TGT CAT CAA CAG CA-3' |

In addition, primers shown in Table 4 were prepared from the 5'-terminus, and full length cDNA encoding northern shrimp cathepsins L1 and L2 were isolated from the single stranded cDNA described above.

TABLE 4

Primers used for cloning the full length cDNAs

Nucleotide sequence

L1-F  5'-TGA GTC AGT TCT GCT CAA CTC TGA TAC G-3'

L2-F  5'-CAC TTT AGC AAG ATG AGG TCT CTG-3'

The determined base sequences and deduced amino acid sequences of northern shrimp cathepsins L1 and L2 are each shown in FIG. 1 (SEQ ID: 1 and 2) and FIG. 2 (SEQ ID: 3 and 4), respectively. N-terminal portion of northern shrimp cathepsin L1 excluding the estimated signal sequence (residues 1 to 15: Met to Ala) and prosequence (16 to 105: Ser to Ala) fully matched the N-terminal amino acid sequence of the purified enzyme. Bases encoding the signal sequence of northern shrimp cathepsin L1 are positions 29 to 73 in SEQ ID: 1. Bases encoding the prosequence are positions 74 to 343 in SEQ ID: 1 and FIG. 1. In addition, the estimated signal sequence of cathepsin L2 is Met to Val: residues 1 to 14, and estimated prosequence is Ser to Met: residues 15 to 106. Bases encoding these sequences positions 13 to 54 and positions 55 to 330 in SEQ ID: 3, respectively.

The homology in amino acid sequences between northern shrimp pro-cathepsins L1 and L2 and cathepsin L of other organisms is shown in Table 5.

As is clear from FIG. 8, catalyst groups Cys, His, and Asn of northern shrimp cathepsins L1 and L2 are conserved, and they are cysteine proteases belonging to the papain superfamily. The locations of S—S bonds are also conserved. By creating a phylogenetic tree by neighbor-joining method (FIG. 9), it can also be seen that both L1 and L2 are cathepsin L-like enzymes.

TABLE 5

Comparison to cathepsin L of other organisms

| | Homology (%) | |
|---|---|---|
| | Northern shrimp cathepsin L1 | Northern shrimp cathepsin L2 |
| Northern shrimp cathepsin L2 | 55 | — |
| Homarus americanus 1 | 55 | 57 |
| Homarus americanus 2 | 57 | 55 |
| Homarus americanus 3 | 55 | 53 |
| Nephrops norvegicus 1 | 57 | 54 |
| Nephrops norvegicus 2 | 53 | 56 |
| Penaeus vannamei 1 | 52 | 52 |
| Penaeus vannamei 2 | 54 | 51 |
| Bombyx mori | 52 | 48 |
| Drosophila melanogaster | 54 | 47 |
| Mus musculus | 47 | 45 |
| Rattus norvegicus | 47 | 44 |
| Bos taurus | 47 | 46 |
| Homo sapiens | 47 | 43 |

Northern shrimp pro-cathepsin L1 showed the highest homology with Cys protease 2 of American lobster (57%) (Table 5). Northern shrimp pro-cathepsin L2 showed the highest homology with Cys protease 1 of American lobster (57%) (Table 5).

EXAMPLE 4

Separation and Purification of Cathepsin L-like Enzyme from Frozen Northern Shrimp Samples <Crude Extracts of Northern Shrimp Cathepsin L1>

All purification steps were carried out at 4° C. Hepatopancreas frozen at −80° C. were partially thawed, 2 volumes of 50 mM Tris-HCl (pH 7.5, containing 150 mM NaCl and 3 mM $NaN_3$) was added and homogenized for 5 minutes with Polytron Homogenizer. Next, 1/5 volume of tetrachloromethane was added with slow stirring, centrifugated (19,000 g, 30 minutes), and lipids were extracted into tetrachloromethane which was the lower layer. Delipidated supernatant was used as crude extract.

<Purification of Northern Shrimp Cathepsin L1-like Protease>

The crude extract was fractionated with 25 to 70% (v/v) cold acetone and centrifugated for 15 minutes at 19,000×g. The obtained precipitate was redissolved in 50 mM Tris-HCl (pH 7.5, containing 50 mM NaCl) (buffer 1), and dialyzed overnight against the same buffer 1. The dialyzed solution was filtered with 0.45 μm filter and subjected to Q-Sepharose ion exchange column (1.6×40 cm Amersham Pharmacia Biotech) equilibrated with the same buffer 1. The column was washed with the same buffer, and the bound protein was eluted with a linear gradient of NaCl in the range of 0 to 0.5 M.

The proteolytic activities of the fractions were measured with Z-Phe-Arg-MCA, Z-Arg-Arg-MCA, and gelatin zymography.

The fraction showing high activity towards Z-Phe-Arg-MCA but showing almost no activity towards Z-Arg-Arg-MCA was collected, dialyzed against 50 mM Tris-HCl (pH 7.5, containing 150 mM NaCl) (buffer 2), and then concentrated by ultrafiltration using Biomax-5K Ultrafree (Millipore). The collected concentrated fraction was loaded onto Superdex 75 pg gel filtration column (1.6×100 cm, Amersham Pharmacia Biotech) equilibrated with buffer 2, and eluted at a flow rate 0.4 ml/min.

The fraction having activity towards Z-Phe-Arg-MCA was collected and dialyzed against 10 mM potassium phosphate buffer (pH 6.8). The dialyzed solution was loaded onto Bio-Scale CHT 10-I hydroxyapatite (1.2×8.8 cm, Bio-Rad) column equilibrated with the same buffer. Non-specifically bound protein was washed off, and the bound protein was eluted using potassium phosphate buffer (pH 6.8) with a linear gradient of 10 to 400 mM.

N-terminal amino acid sequence was identified, and the protein was confirmed to be L1.

<Cathepsin L-like Enzyme Assay>

Enzymatic activity was assayed at 25° C. using intramolecularly quenched MCA (methyl coumarylamide) substrates in a buffer containing 100 mM sodium acetate, pH 6.0, 100 mM NaCl, 2 mM DTT, 2 mM EDTA and 0.01% Brij-35. The substrate solution was prepared in dimethyl sulfoxide at a concentration of 20 mM. Hydrolysis was initiated by adding the enzyme diluted with the same buffer. Enzymatic activity was determined by measuring fluorescence intensity of the released 7-amino-4-methylcoumarin (AMC) at an excitation wavelength of 380 nm and an emission wavelength of 460 nm.

<Substrate Specificity Assay>

The substrate specificity of S2 subsite was measured using various dipeptidic MCA or tripeptidic MCA substrates, under pseudo first-order conditions (pseudo first-order as used herein means condition utilizing a substrate concentration which is far below the estimated $K_m$ wherein initial rate $v_0$ is directly proportional to $k_{cat}/K_m$ value). The results are shown in FIG. 11.

The following fluorescent peptide substrates were used as substrates: Z-Phe-Arg-MCA, Z-Arg-Arg-MCA, Z-Pro-Arg-MCA, Z-Val-Val-Arg-MCA, Z-Leu-Leu-Arg-MCA, Z-Phe-Val-Arg-MCA, H-Arg-MCA and Z-Arg-MCA.

Figure 11:
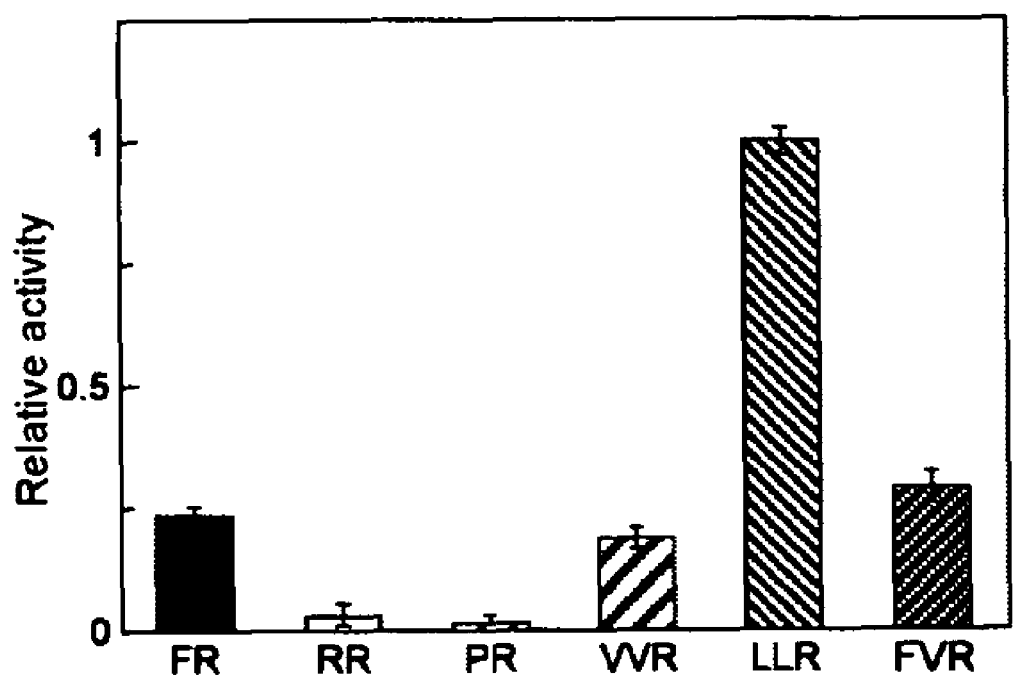

From FIG. 11, it can be seen that north shrimp cathepsin L1 cleaves with high specificity synthetic substrates having non-aromatic hydrophobic residue at P2 position (numbering representation used in Schechter and Berger, 1967, On the size of the active site in proteinases, I. Papain. Biochem. Biophys. Res. Commun. 27, 157-162). This specificity pattern was similar to those of cathepsins K and S, and both cathepsins are more specific to Leu than Phe at this position. On the other hand, cathepsin L is more specific to Phe than Leu.

Unlike cathepsins K and S however, north shrimp cathepsin L1 selectively accepts Val compared to Phe at P2 position.

<Effects of Inhibitors>

Enzyme solution was pretreated with any one of inhibitors E64 (L-trans-epoxysuccinyl-leucyl-agmatine), Z-Phe-Phe-CHN$_2$, Z-Phe-Tyr(t-Bu)-CHN$_2$, leupeptin, antipain, PMSF (phenylmethylsulfonyl fluoride), and 1,10-phenanthroline in a buffer (containing 100 mM sodium acetate, 2 mM DTT, 2 mM EDTA, and 0.05% Triton X-100). Residual enzymatic activity was then measured with fluorescent substrate Z-Phe-Arg-MCA. The final concentrations of the enzymes and the substrate were 1 nM and 100 µM, respectively. The residual enzymatic activity was measured with the method described above.

The results are shown in Table 6.

TABLE 6

| Compound | Concentration | Residual activity (%) |
|---|---|---|
| Control | | 100% |
| E64 | 0.1 µM | 0 |
| | 1 µM | 0 |
| Cathepsin L inhibitor | | |
| Z-Phe-Phe-CHN$_2$ | 1 µM | 78 |
| | 10 µM | 55 |
| Z-Phe-Tyr(t-Bu)-CHN$_2$ | 1 µM | 94 |
| | 10 µM | 86 |
| Serine/cysteine protease inhibitor | | |
| Leupeptin | 1 µM | 0 |
| | 10 µM | 0 |
| Antipain | 1 µM | 0 |
| | 10 µM | 0 |
| Serine protease inhibitor | | |
| PMSF | 1 mM | 100 |
| | 10 mM | 100 |
| Metalloprotease inhibitor | | |
| 1,10-Phenanthroline | 1 mM | 99 |
| | 10 mM | 98 |

As shown in Table 6, northern shrimp cathepsin L1 shows typical cysteine protease inhibitory profile. Northern shrimp cathepsin L1 was strongly inhibited by cysteine protease inhibitor E64, even at a concentration of 0.1 µM. L1 was also strongly inhibited by leupeptin and antipain, which are inhibitors against both of cysteine protease and serine protease.

Although Z-Phe-Phe-CHN$_2$ is an effective inhibitor of cathepsin L, it is known to slightly inhibit cathepsins B and S as well. In addition, Z-Phe-Tyr(t-Bu)-CHN$_2$ is an inhibitor specific to cathepsin L.

However, Z-Phe-Phe-CHN$_2$ and Z-Phe-Tyr(t-Bu)-CHN$_2$ did not inhibit the present enzyme activity so much. Inhibitors specific to serine protease and metalloprotease also did not have inhibitory activity.

From the above, it can be concluded that the north shrimp cathepsin L1 of the present invention differs both in its specificity and inhibition by inhibitors, compared to conventionally known cathepsin L-like proteolytic enzymes. It can also be concluded that it is a completely new enzyme.

EXAMPLE 5

Expression of Northern Shrimp Cathepsin L2

Gene encoding northern shrimp cathepsin L2 (northern shrimp cysteine protease: NsCys) was heterologously expressed in methylotrophic yeast *Pichia pastoris*, using EasySelect™ Echo-Adapted™ Pichia Expression Kit (Invitrogen).

cDNA of 924 bp encoding the full-length precursor of northern shrimp cathepsin L2 (NsCys) excluding its signal peptide was amplified by PCR, and subcloned into pUniD/V5-His-TOPO vectors in the kit according the protocols of the kit. The obtained vectors were subjected to recombination by plasmid fusion via Cre recombinase into *P. pastoris* shuttle vector pPICZα-E so that the cDNA of northern shrimp cathepsin L2 (NsCys) is placed downstream of the yeast α-conjugation factor secretion signal.

The fused plasmid vector was linearlized with restriction enzyme Pme I, and then *P. pastoris* KM71H strain (arg4 aox1: :ARG4) was transformed by electroporation (GenePulser, Bio-Rad). Positive transformants with multiple copies of northern shrimp cathepsin L2 (NsCys) integrated therein were selected by raising the zeocin concentration in the medium containing yeast extract, peptone extract, and sorbitol (YPDS) to 2000 µg/ml. A single colony of high productive clones was selected for large-scale production of recombinant proteins, and pure preparations of northern shrimp cathepsin L2 (northern shrimp cysteine protease: NsCys) were obtained with only a single-step gel filtration chromatography from concentrated medium.

*P. pastoris* clones were inoculated to 1 liter of GCM (glycerol complex medium) prior to the induction of expression and cultivated for 4 days at 30° C. under aerobic condition. The cells were centrifuged at room temperature and 3000×g for 5 minutes, and collected. Expression was induced in 100 ml of BMM medium (buffered Minimal Methanol medium) or MM medium (Minimal Methanol medium). Methanol was added daily at a final concentration of 0.75%, to avoid a loss from the medium by evaporation. To confirm expression, samples were collected everyday, centrifuged at 4° C. and 12000×g for 20 minutes, and the supernatant was subjected to SDS-PAGE using polyacrylamide slab gel with 4 to 20% gradient.

<Purification of Recombinant Protein>

The supernatant of the medium containing no cells was concentrated to approximately 10 ml at 4° C. by ultrafiltration using YM-10 filter (Amicon). The concentrate was dialyzed against 50 mM Tri-HCl (containing 150 mM NaCl). The dialysate was subjected to gel filtration chromatography using Superdex 75 pg column (1.6×100 cm) equilibrated with the same buffer. The protein was eluted using FPLC system at a flow rate of 0.3 ml/min. The fractions were measured for enzyme activity using Z-Phe-Arg-MCA, and the fraction showing the highest activity was further analyzed with SDS-PAGE and zymography to confirm the uniformity of purification degree. Gelatin zymography was utilized using slightly modified Heussen and Dowdle method.

Electrophoresis was carried out at 4° C. using 15% polyacrylamide slab gel containing 0.1% gelatin. Following electrophoresis, SDS was removed by washing in 2.5% Triton-X twice for 30 minutes each. The gel was incubated at room temperature for 3 hours in enzymatic reactive solution (100 mM sodium acetate, pH 5.5, 100 mM NaCl, 2 mM DTT, 2 mM EDTA and 0.01% Brij), stained with Coomassie Brilliant Blue R250, and destained with 10% acetic acid.

The results are shown in FIG. 12 (reference 1, FIG. 5).

N-terminal amino acid sequence of the 30-KDa protein from FIG. 12A (lane 2) was identified. This matched the N-terminal amino acid sequence of mature northern shrimp cathepsin L2 (NsCys) deduced from the base sequence.

<Determination of Protein Concentration>

The concentration of the purified recombinant northern shrimp cathepsin L2 (NsCys) was measured by Bradford method using bovine serum albumin as a standard. To investigate the kinetics of shrimp protease, molar amount of enzyme was measured using Barrett and Kirschke by titration of active site with E-64.

<Enzyme Activity>

Measurement of enzyme activity was carried out as in Example 4.

<pH and Thermal Dependency of Activity and Stability>

The pH activity profile of recombinant northern shrimp cathepsin L2 (NsCys) was measured with substrate concentration of 10 μM under pseudo first-order conditions as described above.

The following buffers were used: 100 mM sodium citrate buffer for pH 3.0 to 6.0, 100 mM sodium phosphate buffer for pH 6.0 to 8.0, and 100 mM sodium borate buffer for pH 8.0 to 11.0. Each pH buffer further contains 2 mM DTT, 2 mM EDTA, and 300 mM NaCl.

Enzyme was incubated at 25° C. for 30 minutes in these buffers to determine the pH stability. Residual activity was measured using fluorescent substrates described above.

The results are shown in FIG. 13. Cathepsin L of mammals are completely inactive or show very low activity in alkaline range, but northern shrimp cathepsin L2 (NsCys) of the present invention maintains approximately 80% activity even at pH 8.5.

To measure the effect of temperature on the activity of northern shrimp cathepsin L2 (NsCys) to hydrolyze Z-Pro-Arg-MCA, buffers containing the substrate were preincubated at different temperatures for 10 minutes, and then the enzyme solution was added. The reaction was carried out for 5 minutes, and the change in fluorescence was recorded as described above. For thermal stability, enzyme solution was treated at 30 to 60° C., samples were collected at certain intervals, immediately cooled on ice, and residual activity towards Z-Pro-Arg-MCA was measured at 25° C.

The results are shown in FIG. 14.

<Substrate Specificity Assay>

Substrate specificity was measured as in Example 4. The results are shown in FIG. 15.

In general, cathepsins L and S prefer substrates with Phe and Leu having bulky hydrophobic side chains to substrates with Val having small β-branching chain at P2 position. In contrast, in Northern shrimp cathepsin L2 (NsCys) preference order for Leu over Val has been reversed. In addition, unlike other known cathepsins, affinity towards Phe is 10 times higher than towards Pro. Cathepsin K of mammals prefers Pro at P2 as well, although it is different in that it similarly accepts Leu as P2 residue and has substantial affinity toward Phe as well.

<Degradation of Glucagon>

One μM of glucagon sample was degraded at 25° C. for 4 hours in 100 mM sodium acetate buffer containing 100 mM NaCl, 2 mM DTT, and 0.01% Brij-35 (pH 6.0), by 12.5 nM of recombinant northern shrimp cathepsin L2 (NsCys). The sample was acidified with 15% acetic acid and the obtained peptide fragments were immediately separated by reverse phase HPLC (ODS-120A column (25×0.4 cm, Tosoh)). The column was washed with water containing 0.1% trifluoroacetic acid until absorbance at 215 nm reached the baseline, and elution was carried out using 95% acetonitrile containing 0.1% trifluoroacetic acid, with a linear gradient of 0 to 60% at a flow rate of 1.0 ml/min.

Eluates corresponding to each absorbance peak at 215 nm were collected, dried under vacuum, and subjected to Protein Sequencer Model 476A from Applied Biosystems.

The results are shown in FIG. 16.

Although Pro is not contained in glucagon, the result matched the results from degradation of synthetic substrates. The preference of residues at P2 position was in the order of Val, Thr, and Ala. The fact that there were no fragments having Leu at P2 indicates that its affinity is very low towards Leu.

<Digestion of Collagen>

The degradation of type I collagen containing large amounts of Pro was tested.

Porcine skin acid-soluble type I collagen was diluted with 100 mM sodium acetate buffer (pH 6.0, containing 150 mM NaCl, 2 mM DTT, and 2 mM EDTA) to a concentration of 2.5 μM and treated with 125 nM northern shrimp cathepsin L2 (NsCys) in the presence or absence of 10 μM E-64.

The samples were collected at a predetermined interval, immediately added to SDS-PAGE sample buffer, and boiled for 5 minutes. Collagenolysis was confirmed by Coomassie Blue staining using 4 to 20% gradient gel (TEFCO).

The results are shown in FIG. 17.

The results are compared with those of known cysteine protease. The degradation of type I collagen was found to be very high.

The present invention provides novel collagenolytic cathepsin L-like enzyme derived from northern shrimp. The present enzyme can be obtained from hepatopancreas of northern shrimp, or by cultivating host cells transformed by introducing the gene encoding the present enzyme. The enzyme of the present invention can be usefully utilized in a broad range of fields such as food products, cosmetics, and medicaments.

The present application is an application claiming priorities of JP Patent Application (Shutsugan) 2002-175773 filed on Jun. 17, 2002 to Japan Patent Office, and U.S. provisional application 60/471733 filed by the present inventors on May 20, 2003 to United States Patent and Trademark Office. The present invention incorporates the contents of both applications herein by reference.

What is claimed is:

1. A purified mature cathepsin cysteine protease derived from northern shrimp comprising an amino acid sequence at least 90% identical to the sequence of amino acids from position 107 through position 323 of SEQ ID NO:4, wherein said protease has the following properties:
   (1) a molecular weight of approximately 30 KDa;
   (2) an optimal pH of approximately 7 to 8;
   (3) an optimal temperature of approximately 35° C.; and
   (4) collagenolytic activity.

2. The purified mature protease of claim 1 comprising an amino acid sequence at least 95% identical to the sequence of amino acids from position 107 through position 323 of SEQ ID NO:4.

3. The purified mature protease of claim 1 wherein the mature protease comprises the amino acid sequence from position 107 through position 323 of SEQ ID NO:4.

4. The purified mature protease of claim 1 wherein the mature protease consists of the amino acid sequence from position 107 through position 323 of SEQ ID NO:4.

5. A purified mature protease having the activity of a cathepsin cysteine protease comprising an amino acid sequence having at least 90% identity to the sequence of amino acids from position 107 through position 323 of SEQ ID NO:4, wherein said protease has collagenolytic activity.

6. The purified mature protease of claim 5 comprising an amino acid sequence having at least 95% identity to the sequence of amino acids from position 107 through position 323 of SEQ ID NO:4, wherein said protease has collagenolytic activity.

7. A purified proprotease having the activity of a cathepsin cysteine protease with collagenolytic activity upon activation, comprising an amino acid sequence having at least 90% identity to the sequence of amino acids from position 15 through position 323 of SEQ ID NO:4.

* * * * *

SEQUENCE LISTING

<160> NUMBER OF SEQ ID NOS: 12

<210> SEQ ID NO 1
<211> LENGTH: 1246
<212> TYPE: DNA
<213> ORGANISM: Northern shrimp(Pandalus eous)

<400> SEQUENCE: 1

```
tgagtcagtt ctgctcaact ctgatacgat gaaggttctt cttttcctgt gtggtctggc    60
catagtcgcc gctagtgaat gggaaaactt caagttgacc catgctaaag tttacaccca   120
tggcaaggaa gatctttaca ggaggtccat ctttgagaac aaccagaagg ttgtcgagga   180
acacaatgaa cgattccgtc agggacttgt caccttcgac ctcaagatga acagattcgg   240
agatatgacg acagaggagt ttgtatccca gatgaccggg ctcaacaaag tagagaggac   300
cgttggtaag gtgttcgctc actaccctga agtagaaagg gctgacactg ttgactggag   360
agacaaagga gctgtgaccc cagttaagga tcagggtcag tgtggatcat gctgggcctt   420
ctctaccact ggagctctgg aaggagcaca tttcctgaaa cacggcgatt tagtcagtct   480
gtccgaacaa aatctggtcg attgctcaac tgagaacagt ggctgtaacg gcggtgtggt   540
ccaatgggcc tacgactaca tcaagtccaa aacggaatt gatactgaat cttcatacccc   600
ctacgaagct caagatttaa cttgtcgatt cgacgctgca cacgttggtg ctaccgttac   660
tggatacgca gatatccctt atgctgatga agtgacccag gcctcagctg tccatgatga   720
tggtccagtc agcgtctgta ttgatgctgg acacaattcc ttccagttgt acagctcagg   780
tgtgtactac gagcctaact gcaatcctag ctctatcaac cacgctgtgt tgcccgtagg   840
atacggaaca gaggaaggca gtgactactg gctcatcaag aactcttggg aactggctg    900
gggtctgagt ggatacatga agctcacaag gaacaagagc aatcattgtg gtgtcgccac   960
ccaatcttgt taccctaatg tctaagagct caatttaaga catggttttc cacttaaaca  1020
acggaggtaa tgtttaacca tttcaaaaac acctcaggaa agccttatgg ataaaagtaa  1080
tggatatctt caaacaattt tccactgaat tttcttgtgt gacgataaaa catctacttc  1140
cgccatttta agattacacc tgactcaaac tatacatatt aatgtgtgta gcattctagt  1200
agaaaataaa gaaagcatta caaataaaa aaaaaaaaaa aaaaaa                  1246
```

<210> SEQ ID NO 2
<211> LENGTH: 318
<212> TYPE: PRT
<213> ORGANISM: Northern shrimp(Pandalus eous)

<400> SEQUENCE: 2

```
Met Lys Val Leu Leu Phe Leu Cys Gly Leu Ala Ile Val Ala Ala Ser
  1               5                  10                  15

Glu Trp Glu Asn Phe Lys Leu Thr His Ala Lys Val Tyr Thr His Gly
             20                  25                  30

Lys Glu Asp Leu Tyr Arg Arg Ser Ile Phe Glu Asn Asn Gln Lys Val
         35                  40                  45

Val Glu Glu His Asn Glu Arg Phe Arg Gln Gly Leu Val Thr Phe Asp
     50                  55                  60

Leu Lys Met Asn Arg Phe Gly Asp Met Thr Thr Glu Glu Phe Val Ser
 65                  70                  75                  80

Gln Met Thr Gly Leu Asn Lys Val Glu Arg Thr Val Gly Lys Val Phe
             85                  90                  95
```

| | | | | | | | | | | | |
|---|---|---|---|---|---|---|---|---|---|---|---|
|Ala|His|Tyr|Pro|Glu|Val|Glu|Arg|Ala|Asp|Thr|Val|Asp|Trp|Arg|Asp|
| | |100| | | |105| | | |110| | | | | |

Lys Gly Ala Val Thr Pro Val Lys Asp Gln Gly Gln Cys Gly Ser Cys
           115                 120                 125

Trp Ala Phe Ser Thr Thr Gly Ala Leu Glu Gly Ala His Phe Leu Lys
        130                 135                 140

His Gly Asp Leu Val Ser Leu Ser Glu Gln Asn Leu Val Asp Cys Ser
145                 150                 155                 160

Thr Glu Asn Ser Gly Cys Asn Gly Val Val Gln Trp Ala Tyr Asp
                165                 170                 175

Tyr Ile Lys Ser Asn Asn Gly Ile Asp Thr Glu Ser Ser Tyr Pro Tyr
            180                 185                 190

Glu Ala Gln Asp Leu Thr Cys Arg Phe Asp Ala Ala His Val Gly Ala
            195                 200                 205

Thr Val Thr Gly Tyr Ala Asp Ile Pro Tyr Ala Asp Glu Val Thr Gln
        210                 215                 220

Ala Ser Ala Val His Asp Asp Gly Pro Val Ser Val Cys Ile Asp Ala
225                 230                 235                 240

Gly His Asn Ser Phe Gln Leu Tyr Ser Ser Gly Val Tyr Tyr Glu Pro
                245                 250                 255

Asn Cys Asn Pro Ser Ser Ile Asn His Ala Val Leu Pro Val Gly Tyr
            260                 265                 270

Gly Thr Glu Glu Gly Ser Asp Tyr Trp Leu Ile Lys Asn Ser Trp Gly
            275                 280                 285

Thr Gly Trp Gly Leu Ser Gly Tyr Met Lys Leu Thr Arg Asn Lys Ser
        290                 295                 300

Asn His Cys Gly Val Ala Thr Gln Ser Cys Tyr Pro Asn Val
305                 310                 315

<210> SEQ ID NO 3
<211> LENGTH: 1242
<212> TYPE: DNA
<213> ORGANISM: Northern shrimp(Pandalus eous)

<400> SEQUENCE: 3

```
cactttagca agatgaggtc tctgtttctt atccttctcg ggctggctgc ggtctccgcc     60
attggagaat gggaaaactt caagacgaag tttggcaaga agtatgccaa ctcagaagag    120
gagagtcaca gaatgtctgt tttcatggac aaactgaagt tcattcagga gcacaatgaa    180
cgatacgata agggagaagt cacttattgg ctgaaaatca caacttctc cgatttgacc     240
cacgaagagg tcttggccac caagactgga atgaccagga acgcacaccc tctttccgta    300
ttgcccaaat ctgccccaac cacaccaatg gccgcagacg ttgactggag gaataagggg    360
gctgtcaccc ccgtcaagga tcagggacaa tgcggatcat gctgggcttt ctcagctgtc    420
gccgccttgg aaggagcgca cttcctgaag accggagatt tggtcagcct gtctgaacag    480
aatttggttg actgctcttc gtcttacggt aaccaaggat gtaatggtgg atggccatac    540
caagcttatc aatacatcat tgccaatcgt ggcattgaca ccgaatcgtc ataccettac    600
aaggcaattg atgacaattg ccgatatgat gccggaaaca tcggcgccac cgtcagcagt    660
tatgtcgaac cagcttcagg agatgagtcc gcacttcagc atgctgtcca gaatgaagga    720
cccgtcagcg tctgcattga tgctggtcaa tcatctttcg gtagttacgg aggaggtgtt    780
tactatgaac caaactgcga ttcctggtac gccaaccatg ccgtgacagc cgtcggctac    840
ggcaccgacg ccaacggagg agattactgg atcgtcaaga actcgtgggg tgcatggtgg    900
ggagagagtg gctacatcaa gatggccaga aacagggaca caactgtgc cattgctacc    960
```

```
tatagtgtct accctgttgt ttaagatctt ttattgacac tcacaatgat tttctttcca    1020
tcatttatca ttggggaact tttaatattc atttggggtt ttcatttgat attttgtgta    1080
agtctcagtc aatcccatta gacatgtttt gttacggtgg attcttaagt caacctttga    1140
atcaaacact tttgtcaaat tacaatgaac acatccaaca gatgatgata catatgaaaa    1200
taaagataca acagataaaa aaaaaaaaaa aaaaaaaaaa aa                       1242
```

<210> SEQ ID NO 4
<211> LENGTH: 323
<212> TYPE: PRT
<213> ORGANISM: Northern shrimp(Pandalus eous)

<400> SEQUENCE: 4

```
Met Arg Ser Leu Phe Ile Leu Leu Gly Leu Ala Ala Val Ser Ala
 1               5                   10                  15

Ile Gly Glu Trp Glu Asn Phe Lys Thr Lys Phe Gly Lys Lys Tyr Ala
            20                  25                  30

Asn Ser Glu Glu Glu Ser His Arg Met Ser Val Phe Met Asp Lys Leu
        35                  40                  45

Lys Phe Ile Gln Glu His Asn Glu Arg Tyr Asp Lys Gly Glu Val Thr
    50                  55                  60

Tyr Trp Leu Lys Ile Asn Asn Phe Ser Asp Leu Thr His Glu Glu Val
65                  70                  75                  80

Leu Ala Thr Lys Thr Gly Met Thr Arg Arg His Pro Leu Ser Val
                85                  90                  95

Leu Pro Lys Ser Ala Pro Thr Thr Pro Met Ala Ala Asp Val Asp Trp
            100                 105                 110

Arg Asn Lys Gly Ala Val Thr Pro Val Lys Asp Gln Gly Gln Cys Gly
        115                 120                 125

Ser Cys Trp Ala Phe Ser Ala Val Ala Ala Leu Glu Gly Ala His Phe
    130                 135                 140

Leu Lys Thr Gly Asp Leu Val Ser Leu Ser Glu Gln Asn Leu Val Asp
145                 150                 155                 160

Cys Ser Ser Ser Tyr Gly Asn Gln Gly Cys Asn Gly Gly Trp Pro Tyr
                165                 170                 175

Gln Ala Tyr Gln Tyr Ile Ile Ala Asn Arg Gly Ile Asp Thr Glu Ser
            180                 185                 190

Ser Tyr Pro Tyr Lys Ala Ile Asp Asp Asn Cys Arg Tyr Asp Ala Gly
        195                 200                 205

Asn Ile Gly Ala Thr Val Ser Ser Tyr Val Glu Pro Ala Ser Gly Asp
    210                 215                 220

Glu Ser Ala Leu Gln His Ala Val Gln Asn Glu Gly Pro Val Ser Val
225                 230                 235                 240

Cys Ile Asp Ala Gly Gln Ser Ser Phe Gly Ser Tyr Gly Gly Gly Val
                245                 250                 255

Tyr Tyr Glu Pro Asn Cys Asp Ser Trp Tyr Ala Asn His Ala Val Thr
            260                 265                 270

Ala Val Gly Tyr Gly Thr Asp Ala Asn Gly Gly Asp Tyr Trp Ile Val
        275                 280                 285

Lys Asn Ser Trp Gly Ala Trp Trp Gly Glu Ser Gly Tyr Ile Lys Met
    290                 295                 300

Ala Arg Asn Arg Asp Asn Asn Cys Ala Ile Ala Thr Tyr Ser Val Tyr
305                 310                 315                 320

Pro Val Val
```

```
<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
gcatcaatac agacgctgac                                               20

<210> SEQ ID NO 6
<211> LENGTH: 21
<212> TYPE: DNA
<213> ORGANISM: Artificial Sequence
<220> FEATURE:
<223> OTHER INFORMATION: Primer

<400> SEQUENCE: 6
catcagcata agggatatct g                                             21

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
aacgtgtgca gcgtcgaatc                                               20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
gtctcatctc cttcggttac                                               20

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
accttgaatg gtggcaccga                                               20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
cgcacttgtc atcaacagca                                               20

<210> SEQ ID NO 11
<211> LENGTH: 28
<212> TYPE: DNA
<213> ORGANISM: Artificial Sequence
<220> FEATURE:
<223> OTHER INFORMATION: Primer
```

```
<400> SEQUENCE: 11
tgagtcagtt ctgctcaact ctgatacg                                           28

<210> SEQ ID NO 12
<211> LENGTH: 24
<212> TYPE: DNA
<213> ORGANISM: Artificial Sequence
<220> FEATURE:
<223> OTHER INFORMATION: Primer

<400> SEQUENCE: 12
cactttagca agatgaggtc tctg                                               24
```